United States Patent
Fujita et al.

(10) Patent No.: US 9,855,339 B2
(45) Date of Patent: Jan. 2, 2018

(54) PHARMACEUTICAL PREPARATION OF CAMPTOTHECIN-CONTAINING POLYMER DERIVATIVE

(71) Applicant: Nippon Kayaku Kabushiki Kaisha, Tokyo (JP)

(72) Inventors: Shinya Fujita, Tokyo (JP); Shin Aoki, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/515,295

(22) PCT Filed: Oct. 16, 2015

(86) PCT No.: PCT/JP2015/079314
§ 371 (c)(1),
(2) Date: Mar. 29, 2017

(87) PCT Pub. No.: WO2016/103867
PCT Pub. Date: Jun. 30, 2016

(65) Prior Publication Data
US 2017/0298190 A1   Oct. 19, 2017

(30) Foreign Application Priority Data
Dec. 26, 2014   (JP) .................. 2014-263848

(51) Int. Cl.
| A61K 39/00 | (2006.01) |
| C07D 491/00 | (2006.01) |
| A61K 31/44 | (2006.01) |
| A61K 38/00 | (2006.01) |
| A61K 47/48 | (2006.01) |
| A61K 9/08 | (2006.01) |
| A61K 9/19 | (2006.01) |
| A61K 31/4745 | (2006.01) |
| C08G 81/00 | (2006.01) |

(52) U.S. Cl.
CPC .......... *A61K 47/48207* (2013.01); *A61K 9/08* (2013.01); *A61K 9/19* (2013.01); *A61K 31/4745* (2013.01); *C08G 81/00* (2013.01)

(58) Field of Classification Search
None
See application file for complete search history.

(56) References Cited

U.S. PATENT DOCUMENTS

| 6,815,435 | B2 | 11/2004 | Takahashi et al. |
| 8,334,364 | B2 | 12/2012 | Yamamoto et al. |
| 2005/0215485 | A1 | 9/2005 | Ito et al. |
| 2006/0067910 | A1 | 3/2006 | Kitagawa et al. |
| 2009/0239782 | A1 | 9/2009 | Nakamura et al. |
| 2010/0004403 | A1 | 1/2010 | Kitagawa et al. |
| 2011/0110881 | A1 | 5/2011 | Kataoka et al. |
| 2015/0011715 | A1 | 1/2015 | Nakamura et al. |
| 2016/0279164 | A1 | 9/2016 | Nakamura et al. |

FOREIGN PATENT DOCUMENTS

| EP | 2204398 A1 | 7/2010 |
| JP | 2005-523329 A | 8/2005 |
| WO | 2002/005855 A1 | 1/2002 |
| WO | 2004/039869 A1 | 5/2004 |
| WO | 2008/010463 A1 | 1/2008 |
| WO | 2008/041610 A1 | 4/2008 |
| WO | 2008/056596 A1 | 5/2008 |
| WO | 2009/142328 A1 | 11/2009 |
| WO | 2009/157279 A1 | 12/2009 |

OTHER PUBLICATIONS

International Search Report and Written Opinion dated Nov. 17, 2015 in corresponding PCT application No. PCT/JP2015/079314.
Japanese communication, with English translation, dated Jun. 14, 2016 in corresponding Japanese patent application No. 2016-506023.
Japanese communication, with English translation, dated Sep. 6, 2016 in corresponding Japanese patent application No. 2016-506023.
Gu et al., "SN-38 Loaded Polymeric Micelles to Enhance Cancer Therapy," Nanotechnology, vol. 23, No. 20, 2012.
Kataoka, "Seitai Seigyo Busshitsu no Shinki Hosetsu Tantai to shite no Kobunshi Micelle," Tokyo Seikagaku Kenkyusho Josei Kenkyu Hokokushu, 1995, edition of Heisei 6 Nendo, pp. 48-60, ISSN 1345-4927.
Written Opinion dated Nov. 17, 2015 in corresponding PCT application No. PCT/JP2015/079314.

*Primary Examiner* — Jeffrey T. Palenik
(74) *Attorney, Agent, or Firm* — Nields, Lemack & Frame, LLC

(57) ABSTRACT

Provided is a pharmaceutical preparation composition comprising a polymerized camptothecin derivative which is obtained by bonding a camptothecin derivative to a polymer carrier, and has nanoparticle-forming properties of associating in an aqueous solution, the pharmaceutical preparation composition having enhanced preparation stability. Particularly, a pharmaceutical preparation maintaining nanoparticle-forming properties, which are an important factor, and having an excellent storage stability is provided.
Disclosed is a pharmaceutical preparation comprising a block copolymer in which a polyethylene glycol segment is linked to a polyglutamic acid segment containing a glutamic acid unit having a camptothecin derivative bonded thereto, the pharmaceutical preparation capable of forming associates in an aqueous solution. When the pharmaceutical preparation is made into an aqueous solution containing the camptothecin derivative at a concentration of 1 mg/mL, the pH of the aqueous solution is 2.4 to 7.0, and the change ratio of the associate-forming ability of the pharmaceutical preparation after storage at 40° C. for one week under light-blocked conditions is 50% or less.

6 Claims, No Drawings

PHARMACEUTICAL PREPARATION OF CAMPTOTHECIN-CONTAINING POLYMER DERIVATIVE

TECHNICAL FIELD

The present invention relates to a pharmaceutical preparation composition of a polymerized camptothecin derivative produced by bonding a camptothecin derivative to a polymer carrier, the pharmaceutical preparation composition having enhanced preparation stability. The polymerized camptothecin derivative has a property by which a plurality of molecules of the derivative become associative in an aqueous solution, thereby forming nanoparticles. The present invention relates to a technology relating to a pharmaceutical preparation containing a polymerized camptothecin derivative having such nanoparticle-forming properties, the pharmaceutical preparation having excellent storage stability of maintaining the nanoparticle-forming properties for a long time.

BACKGROUND ART

In order to effectively manifest the efficacy of a pharmaceutical product, it is required to cause a pharmacologically active compound to act on an appropriate site in the body at an appropriate concentration for an appropriate length of time. Particularly, when systematically administered by intravenous administration or the like, a cytotoxic antitumor agent is widely distributed over the whole body and exhibits cell proliferation inhibitory action. In this case, it is reported that since cells are subjected to the pharmacological action without distinction between cancer cells and normal cells, serious side effects are brought about due to the action on the normal cells. Therefore, in order to reduce side effects, a technology of transporting the antitumor agent to a tumor lesion is important. Thus, there is a demand for a method for controlling the pharmacokinetics in order to selectively transport an antitumor agent to a tumor tissue and to cause the antitumor agent to act at an appropriate drug concentration for an appropriate time for manifesting the effect of the drug.

As a method for controlling the pharmacokinetics, a method of utilizing the pharmacokinetic characteristics based on the molecular weight is known. That is, when a biocompatible polymer material is intravascularly administered, renal excretion is suppressed, and a long half-life in blood is maintained. Furthermore, although recovery mechanism of polymer materials is not sufficiently constructed in the tumor tissue, it is known that tumor tissues have high tissue permeability of polymer materials, and that polymer materials are distributed and concentrated in tumor tissues at relatively high concentrations. Thus, polymerized antitumor agent derivatives in which a biocompatible polymer material is used as a polymer carrier and an antitumor agent is bonded to this polymer carrier, has been developed.

As such polymerized antitumor agents, polymer derivatives of antitumor agents have been reported, in which a block copolymer obtained by linking a polyethylene glycol segment and a polyglutamic acid segment is used as a polymer carrier, and various antitumor agents are bonded to side-chain carboxylic acids of the polyglutamic acid segment. Patent Document 1 discloses a pharmaceutical product in which 7-ethyl-10-hydroxycamptothecin is bonded to the relevant block copolymer. Furthermore, as other antitumor agents, a block copolymer conjugate of a cytidine-based antitumor agent (Patent Document 2), a block copolymer conjugate of combretastatin A-4 (Patent Document 3), a block copolymer conjugate of a HSP90 inhibitor (Patent Document 4), and the like are known. It is stated that these polymerized antitumor agents have enhanced antitumor effects, compared to those low molecular weight antitumor compounds used as active ingredients.

These block copolymer conjugates of antitumor agents are polymerized antitumor agents in which hydroxyl groups of the antitumor agent are bonded to side chain carboxylic acids of the block copolymer through ester bonds. These are prodrugs that exhibit antitumor activity when administered into the body, by cleaving the ester bonds at a constant rate to release the antitumor agent.

Furthermore, these block copolymers having antitumor agents bonded thereto have a physical property by which, when the block region to which the antitumor agent is bonded is hydrophobic, the antitumor agent-bonded region in an aqueous solution exhibits associative properties based on a hydrophobic interaction, and a plurality of the molecules of the block copolymer form associates through aggregation.

Associative aggregates formed by this polymerized antitumor agents may be detected by a light scattering analysis using laser light or the like, and the physical properties of the associative aggregates may be measured by means of the value of light scattering intensity. That is, the physical properties of the associative aggregates may be defined by taking the light scattering intensity as a measured value. For example, the block copolymer having an antitumor agent bonded thereto as described above has a physical property of forming nanoparticles that measure several nanometers to several hundred nanometers in size according to a particle size analysis based on a light scattering analysis method. Furthermore, similarly, in the measurement of the total molecular weight based on light scattering intensity measurement, it may be analyzed that the associative aggregates of the block copolymer having an antitumor agent bonded thereto are associates having a total molecular weight of several millions or more.

A polymerized antitumor agents having such associative properties behaves as nanoparticles in the body, thereby exhibiting pharmacokinetics such as described above, and is distributed at a high concentration in a tumor tissue. Then, the polymerized antitumor agent liberates an antitumor agent, thereby exhibiting a high antitumor effect. Therefore, for these polymerized antitumor agents, the associative properties of forming nanoparticles constitute an important factor for achieving the performance.

A drug-polymer conjugate pharmaceutical product such as described above is a pharmaceutical product that promotes high pharmacological activity and reduces side effects by means of the pharmacokinetics based on the molecular weight of the polymer carrier and by slowly releasing the drug bonded thereto as an active form. Therefore, such a drug-polymer conjugate pharmaceutical product needs to be prepared as a preparation which undergoes less change in the molecular weight of the polymer carrier under storage conditions, that is, a preparation having excellent storage stability with suppressed molecular weight reduction.

As a preparation provided with storage stability for a drug-polymer conjugate pharmaceutical product taken into consideration, for example, Patent Documents 5 and 6 disclose that changes in the molecular weight of the polymer carrier and liberation of the camptothecin derivative are suppressed by producing a conjugate of a polysaccharide having carboxyl groups and a camptothecin derivative into a pharmaceutical preparation including a sugar or a sugar alcohol and a pH adjusting agent.

However, in the drug-polymer conjugate pharmaceutical products described in Patent Documents 5 and 6, the drugs are bonded in a dispersed state to water-soluble polymer carriers, and therefore, it is speculated that the drug-polymer conjugate pharmaceutical products do not form associates in the form of nanoparticles. Thus, the molecular weight of the polymer carrier is considered to function as a performance-achieving factor. For this reason, molecular weight reduction by a chemical decomposition reaction caused by cleavage of chemical bonds of the carrier is a problem to be solved, and this suppression is the purpose of the invention. However, in regard to polymerized antitumor agents based on block copolymers, which employ polymerization by producing nanoparticles from associative aggregates as a performance-controlling factor, a stable pharmaceutical preparation intended to control the nanoparticle-forming ability has not been known.

CITATION LIST

Patent Literature

[Patent Literature 1] WO 2004/39869 A
[Patent Literature 2] WO 2008/056596 A
[Patent Literature 3] WO 2008/010463 A
[Patent Literature 4] WO 2008/041610 A
[Patent Literature 5] WO 2002/005855 A
[Patent Literature 6] JP 2005-523329 A

SUMMARY OF THE INVENTION

Technical Problem

It is an object of the present invention to provide a pharmaceutical preparation composition of a polymerized camptothecin derivative obtained by bonding a camptothecin derivative to a polymer carrier, the pharmaceutical preparation composition having the nanoparticle-forming properties maintained for a long time and having enhanced preparation-related stability. Particularly, it is an important factor in view of performance that the polymerized camptothecin derivative has associative properties, and a plurality of molecules of the polymerized camptothecin derivative form associates by aggregating in an aqueous solution and thus form nanoparticles. It is an object of the invention to provide a pharmaceutical preparation containing a polymerized camptothecin derivative capable of forming nanoparticles, the pharmaceutical preparation having excellent storage stability based on the associate nanoparticle-forming properties as an indicator.

Solution to Problem

The inventors of the present invention found that, in regard to a polymerized camptothecin derivative based on a block copolymer in which a polyethylene glycol segment is linked to a polyglutamic acid segment including a glutamic acid unit having a camptothecin derivative bonded thereto, a pharmaceutical preparation having an excellent storage stability and having controlled nanoparticle-forming properties based on the formation of associates as a result of aggregation of multiple molecules of the polymerized camptothecin derivative is obtained by setting the pH of an aqueous solution of this derivative in a particular pH range. Thus, the inventors completed the invention. That is, the gist of the present specification includes the following inventions.

[1] A pharmaceutical preparation comprising a block copolymer represented by general formula (1), the block copolymer comprising a polyethylene glycol segment linked to a polyglutamic acid segment comprising a glutamic acid unit having a camptothecin derivative bonded thereto:

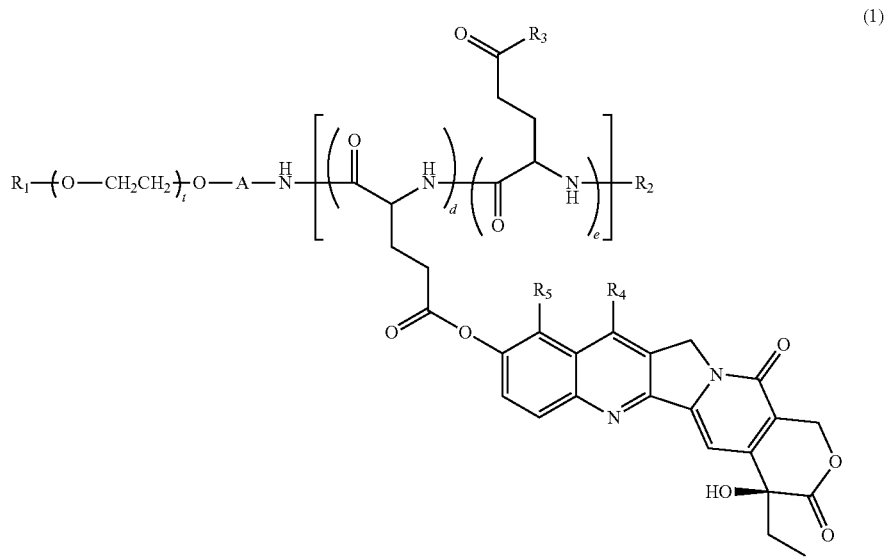

(1)

wherein $R_1$ represents a hydrogen atom or a (C1-C6) alkyl group optionally substituted with a substituent; A represents a (C1-C6) alkylene group; $R_2$ represents any one selected from the group consisting of a hydrogen atom, a (C1-C6) acyl group optionally substituted with a substituent, and a (C1-C6) alkoxycarbonyl group optionally substituted with a substituent; $R_3$ represents a hydroxyl group and/or —N($R_6$)CONH($R_7$); $R_6$ and $R_7$ may be identical or different and each represent a (C1-C8) alkyl group optionally substituted with a tertiary amino group; $R_4$ represents any one selected from the group consisting of a hydrogen atom, a (C1-C6) alkyl group optionally substituted with a substituent, and a silyl group optionally substituted with a substituent; $R_5$ represents a hydrogen atom or a (C1-C6) alkyl group optionally substituted with a substituent; t represents an integer from 45 to 450; d and e each represent an integer, (d+e) represents an integer from 6 to 60; the proportion of d with respect to (d+e) is 1% to 100%, and the proportion of e is 0% to 99%; and the polyglutamic acid segment has a polyglutamic acid segment structure including a glutamic acid unit having the camptothecin derivative bonded thereto and a glutamic acid unit having a $R_3$ group bonded thereto, with the glutamic acid units being each independently arranged in a random manner, wherein a plurality of molecules of the block copolymer form associates in an aqueous solution of the pharmaceutical preparation, wherein, when the pharmaceutical preparation is made into an aqueous solution containing the camptothecin derivative at a concentration of 1 mg/mL, the pH of the aqueous solution is 2.4 to 7.0, and wherein the change ratio of the total molecular weight of the associates of the pharmaceutical preparation obtained after storage of the pharmaceutical preparation at 40° C. for one week under light-blocked conditions is 50% or less.

Furthermore, the pharmaceutical preparation of the present invention may be defined by another preparation stability evaluation.

[2] A pharmaceutical preparation comprising a block copolymer represented by general formula (1), the block copolymer comprising a polyethylene glycol segment linked to a polyglutamic acid segment containing a glutamic acid unit having a camptothecin derivative bonded thereto:

acyl group optionally substituted with a substituent, and a (C1-C6) alkoxycarbonyl group optionally substituted with a substituent; $R_3$ represent a hydroxyl group and/or —N($R_6$)CONH($R_7$); $R_6$ and $R_7$ may be identical or different and each represent a (C1-C8) alkyl group optionally substituted with a tertiary amino group; $R_4$ represents any one selected from the group consisting of a hydrogen atom, a (C1-C6) alkyl group optionally substituted with a substituent, and a silyl group optionally substituted with a substituent; $R_5$ represents a hydrogen atom or a (C1-C6) alkyl group optionally substituted with a substituent; t represents an integer from 45 to 450; d and e each represent an integer, (d+e) represents an integer from 6 to 60; the proportion of d with respect to (d+e) is 1% to 100%, and the proportion of e is 0% to 99%; and the polyglutamic acid segment has a polyglutamic acid segment structure including a glutamic acid unit having the camptothecin derivative bonded thereto and a glutamic acid unit having a $R_3$ group bonded thereto, with the glutamic acid units being each independently arranged in a random manner, wherein a plurality of molecules of the block copolymer form associates in an aqueous solution of the pharmaceutical preparation, wherein, when the pharmaceutical preparation is made into an aqueous solution containing the camptothecin derivative at a concentration of 1 mg/mL, the pH of the aqueous solution is 2.4 to 7.0, and wherein the change ratio of the particle size of the associates of the pharmaceutical preparation measured by a dynamic light scattering method after storage of the pharmaceutical preparation at 40° C. for one week under light-blocked conditions is from 0.25 times to 5 times.

In regard to the block copolymer related to the present invention, in which a polyethylene glycol segment is linked to a polyglutamic acid segment comprising a glutamic acid unit having a camptothecin derivative bonded thereto, since the polyglutamic acid segment having the camptothecin derivative bonded thereto is relatively hydrophobic in the

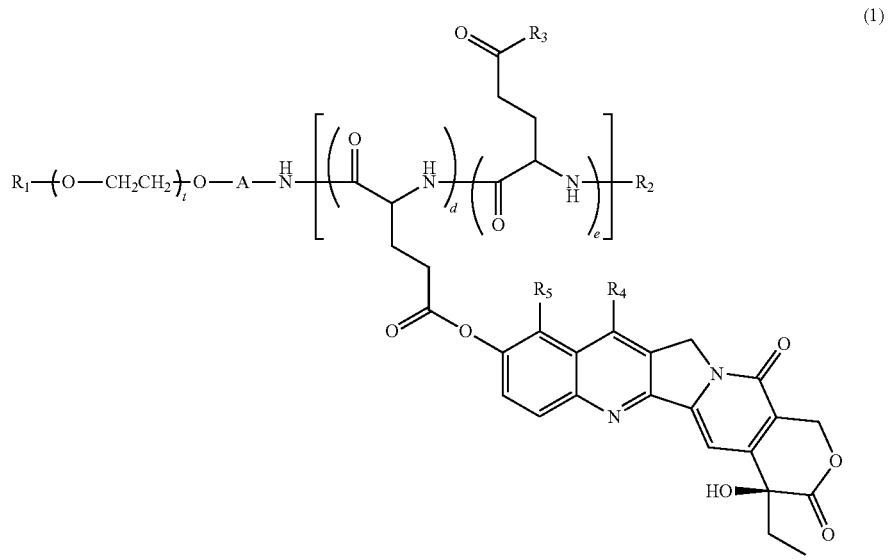

(1)

wherein $R_1$ represents a hydrogen atom or a (C1-C6) alkyl group optionally substituted with a substituent; A represents a (C1-C6) alkylene group; $R_2$ represents any one selected from the group consisting of a hydrogen atom, a (C1-C6)

block copolymer, the block copolymer exhibits associative properties based on a hydrophobic interaction in an aqueous solution, and forms nanoparticles, which are associates formed by aggregation of a plurality of molecules of the block copolymer. This is a pharmaceutical product which exhibits pharmacokinetics based on nanoparticles when administered into the body, and is intended to release the camptothecin derivative therefrom at a constant rate to exhibit pharmacological activity. Therefore, for the block copolymer, which is a polymerized camptothecin derivative, the physical properties of forming nanoparticles through the formation of associates are a key factor for exhibiting the performance.

Furthermore, the pharmaceutical preparation of the present invention may be defined by physical properties combining the above-described items [1] and [2].

[3] A pharmaceutical preparation comprising a block copolymer represented by general formula (1), the block copolymer comprising a polyethylene glycol segment linked to a polyglutamic acid segment containing a glutamic acid unit having a camptothecin derivative bonded thereto:

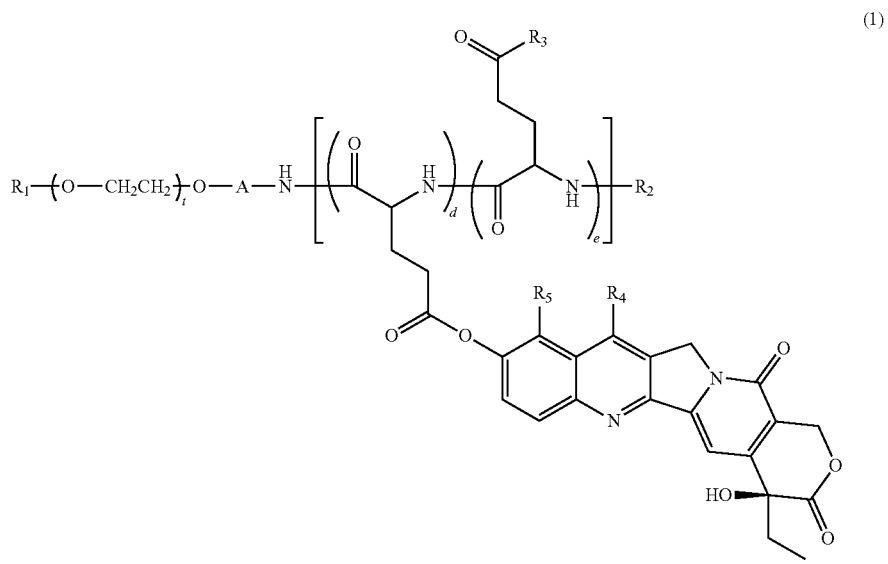

In regard to the associates, the associate-forming properties may be evaluated by measuring the light scattering intensity using laser light. For example, the light scattering intensity may be directly used as a physical property value for the associate-forming properties. Usually, for this block copolymer, a measured value of several thousand cps to several hundred thousand cps is obtained as a light scattering intensity value, and thus the block copolymer is acknowledged to form associates. From this light scattering intensity value, the molecular weight of the associates may be estimated based on polyethylene glycol standard reference materials. According to this measurement method, it is calculated that the block copolymer forms associates having a total molecular weight of several millions or more. On the other hand, according to a particle size analysis based on a dynamic light scattering analysis, the block copolymer has a physical property of forming nanoparticulate bodies having a particle size of several nanometers to several hundred nanometers.

Therefore, the block copolymer is a polymerized camptothecin derivative which, when administered into the body, exhibits specific pharmacokinetics based on the physical properties as nanoparticles to be distributed at a high concentration in tumor tissues, and liberates an antitumor agent there, thereby exhibiting an excellent antitumor effect. Therefore, the physical property of forming nanoparticles through formation of associates is an important factor for exhibiting performance. The present invention enables production of a highly stable pharmaceutical preparation containing the polymerized camptothecin derivative, in which the nanoparticle-forming properties as a key factor in view of performance are well controlled and stably maintained during storage of the preparation.

wherein $R_1$ represents a hydrogen atom or a (C1-C6) alkyl group optionally substituted with a substituent; A represents a (C1-C6) alkylene group; $R_2$ represents any one selected from the group consisting of a hydrogen atom, a (C1-C6) acyl group optionally substituted with a substituent, and a (C1-C6) alkoxycarbonyl group optionally substituted with a substituent; $R_3$ represent a hydroxyl group and/or —N($R_6$)CONH($R_7$); $R_6$ and $R_7$ may be identical or different and each represent a (C1-C8) alkyl group optionally substituted with a tertiary amino group; $R_4$ represents any one selected from the group consisting of a hydrogen atom, a (C1-C6) alkyl group optionally substituted with a substituent, and a silyl group optionally substituted with a substituent; $R_5$ represents a hydrogen atom or a (C1-C6) alkyl group optionally substituted with a substituent; t represents an integer from 45 to 450; d and e each represent an integer, (d+e) represents an integer from 6 to 60; the proportion of d with respect to (d+e) is 1% to 100%, and the proportion of e is 0% to 99%; and the polyglutamic acid segment has a polyglutamic acid segment structure including a glutamic acid unit having the camptothecin derivative bonded thereto and a glutamic acid unit having a $R_3$ group bonded thereto, with the glutamic acid units being each independently arranged in a random manner, wherein a plurality of molecules of the block copolymer form associates in an aqueous solution of the pharmaceutical preparation, wherein, when the pharmaceutical preparation is made into an aqueous solution containing the camptothecin derivative at a concentration of 1 mg/mL, the pH of the aqueous solution is 2.4 to 7.0, wherein the change ratio of the total molecular weight of the associates of the pharmaceutical preparation obtained after storage of the pharmaceutical preparation at 40° C. for one week under light-blocked conditions is 50% or less, and wherein the change ratio of the particle size of the associates of the pharmaceutical preparation measured by a dynamic light scattering method after storage of the pharmaceutical preparation at 40° C. for one week under light-blocked conditions is from 0.25 times to 5 times.

That is, the pharmaceutical preparation of the present invention is a pharmaceutical preparation having excellent storage stability with less change in physical properties, in which formation of nanoparticles, which are associates formed by aggregation of multiple molecules of the block copolymer, is maintained during storage, and the total molecular weight and particle size of the associative properties undergo less change.

[4] The pharmaceutical preparation according to any one of items [1] to [3], wherein the pharmaceutical preparation is a freeze-dried preparation.

The pharmaceutical preparation of the present invention is a desirable dosage form, since it is easy to control and maintain the nanoparticle-forming properties stably by producing the pharmaceutical preparation as a freeze-dried preparation.

[5] The pharmaceutical preparation according to any one of items [1] to [4], wherein the pharmaceutical preparation comprises a pH adjusting agent, and wherein, when the pharmaceutical preparation is made into an aqueous solution containing the camptothecin derivative at a concentration of 1 mg/mL, the pH of the aqueous solution is adjusted to 2.4 to 7.0.

According to the present invention, it is possible to set the relevant pharmaceutical preparation to a particular pH by adding an acidic additive, a basic additive, or a pH adjusting agent that is a mixture of an acidic additive and a basic additive.

[6] The pharmaceutical preparation according to any one of items [1] to [5], further comprising a sugar and/or a polyol.

The present invention is more preferable because a pharmaceutical preparation having more-controlled nanoparticle-forming ability can be provided by adding a sugar and/or a polyol thereto. Furthermore, the present invention is more preferable since, when the pharmaceutical preparation is prepared as a freeze-dried preparation, the dissolution rate at reconstitution of the pharmaceutical preparation into an aqueous solution may be increased.

Effects of Invention

In regard to the block copolymer related to the present invention, in which a polyethylene glycol segment is linked to a polyglutamic acid segment including a glutamic acid unit having a camptothecin derivative bonded thereto, the formation of nanoparticles caused by associative aggregates is an essential performance required for manifesting the efficacy, and it is particularly important that nanoparticles in a desired associated state may be formed. The pharmaceutical preparation of the present invention may provide a pharmaceutical preparation containing as an active ingredient the block copolymer that forms associative aggregates, the pharmaceutical preparation having excellent storage stability. That is, the present invention provides a pharmaceutical preparation with ensured stability in which the block copolymer maintains a desired associated state during the storage of the preparation, and the pharmaceutical preparation aqueous solution used as a pharmaceutical product may be used as a desired associative nanoparticle-forming body. Thus, a pharmaceutical preparation having guaranteed effectiveness as a pharmaceutical product may be provided.

DESCRIPTION OF EMBODIMENTS

The present invention relates to a stabilized pharmaceutical preparation comprising a block copolymer in which a polyethylene glycol segment is linked to a polyglutamic acid segment including a glutamic acid unit having a camptothecin derivative bonded thereto, wherein the associate-forming properties are stably maintained, said pharmaceutical preparation having a small change ratio in the formation of associates after storage of the pharmaceutical preparation at 40° C. for one week under light-blocked conditions, in the case where, when the pharmaceutical preparation is made into an aqueous solution containing the camptothecin derivative at a concentration of 1 mg/mL, the pH of the aqueous solution is adjusted to 2.4 to 7.0. The present invention will be described in detail below. Meanwhile, the associates as used herein may also be referred to as associative aggregates.

The present invention uses a block copolymer in which a polyethylene glycol segment is linked to a polyglutamic acid segment including a glutamic acid unit having a camptothecin derivative bonded thereto, the block copolymer being represented by the following general formula (1):

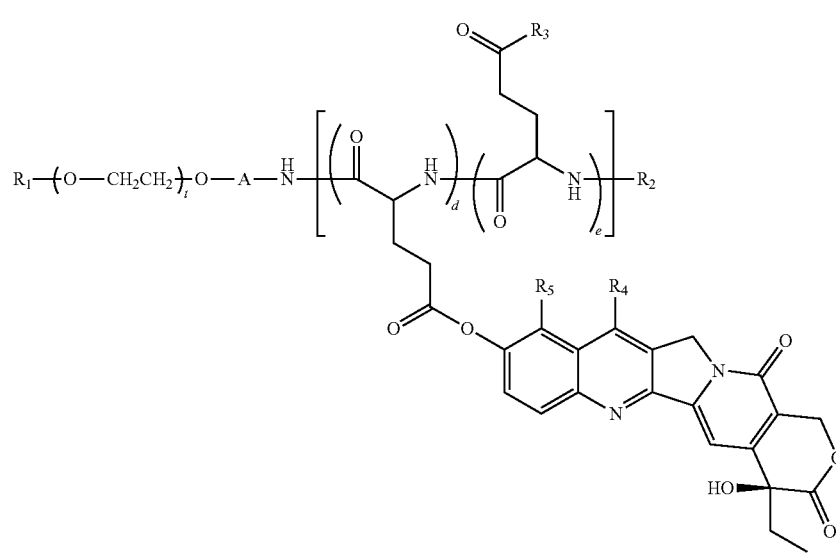

(1)

wherein $R_1$ represents a hydrogen atom or a (C1-C6) alkyl group which may have a substituent; A represents a (C1-C6) alkylene group; $R_2$ represents any one selected from the group consisting of a hydrogen atom, a (C1-C6) acyl group which may have a substituent, and a (C1-C6) alkoxycarbonyl group which may have a substituent; $R_3$ represents a hydroxyl group and/or $N(R_6)CONH(R_7)$; $R_6$ and $R_7$ may be identical or different, and each represents a (C1-C8) alkyl group which may be substituted with a tertiary amino group; $R_4$ represents any one selected from the group consisting of a hydrogen atom, a (C1-C6) alkyl group which may have a substituent, and a silyl group which may have a substituent; $R_5$ represents a hydrogen atom or a (C1-C6) alkyl group which may have a substituent; t represents an integer from 45 to 450; d and e each represent an integer, such that (d+e) represents an integer from 6 to 60, and the proportion of d with respect to (d+e) is 1% to 100%, and the proportion of e is 0% to 99%; and the polyglutamic acid segment have a polyglutamic acid segment structure in which glutamic acid units having the camptothecin derivative bonded thereto, and glutamic acid units having $R_3$ groups bonded thereto are each independently arranged in a random manner.

The block copolymer is a block copolymer in which a polyethylene glycol segment is linked by an appropriate linking group to a polyglutamic acid segment including a glutamic acid unit having a camptothecin derivative bonded to a side chain by an ester bond.

The (C1-C6) alkyl group which may have a substituent with regard to $R_1$ may be a linear, branched or cyclic (C1-C6) alkyl group which may have a substituent. Examples thereof may include a methyl group, an ethyl group, a n-propyl group, an isopropyl group, a n-butyl group, a s-butyl group, a t-butyl group, a n-propyl group, a neo-pentyl group, a cyclopentyl group, a n-hexyl group, and a cyclohexyl group.

Examples of the substituent to be carried may include a mercapto group, a hydroxyl group, a halogen atom, a nitro group, a cyano group, a carbocyclic or heterocyclic aryl group, an alkylthio group, an arylthio group, an alkylsulfinyl group, an arylsulfinyl group, an alkylsulfonyl group, an arylsulfonyl group, a sulfamoyl group, an alkoxy group, an aryloxy group, an acyloxy group, an alkoxycarbonyloxy group, a carbamoyloxy group, a substituted or unsubstituted amino group, an acylamino group, alkoxycarbonylamino group, a ureido group, a sulfonylamino group, a sulfamoylamino group, a formyl group, an acyl group, a carboxyl group, an alkoxycarbonyl group, a carbamoyl group, and a silyl group. The position of substitution on the aromatic ring may be the ortho-position, the meta-position, or the para-position. An amino group, a dialkylamino group, an alkoxy group, a carboxyl group, and a formyl group are preferred.

Preferred examples of $R_1$ may include a methyl group, an ethyl group, a n-propyl group, an isopropyl group, a n-butyl group, a s-butyl group, a t-butyl group, a benzyl group, a 2,2-dimethoxyethyl group, a 2,2-diethoxyethyl group, and a 2-formylethyl group. An unsubstituted linear, branched or cyclic (C1-C4) alkyl group is preferred. A methyl group, an ethyl group, a n-propyl group, an isopropyl group, a n-butyl group, a s-butyl group, a t-butyl group, and the like are particularly preferred.

In regard to general formula (1), it is preferable to use a polyethylene glycol segment in which the polyethylene glycol moiety has a molecular weight of 2 kilodaltons to 20 kilodaltons, and more preferably 4 kilodaltons to 15 kilodaltons. That is, t in general formula (1), which is the number of unit repeated structures of an ethyleneoxy group; $(-OCH_2CH_2)$ group, represents an integer from 45 to 450. Preferably, t represents an integer from 90 to 340. Meanwhile, regarding the molecular weight of the polyethylene glycol segment, the peak top molecular weight that is determined by a GPC method using polyethylene glycol standards is used.

A in general formula (1), which is a linking group that links the polyethylene glycol segment to the polyglutamic acid segment, is a (C1-C6) alkylene group. Examples thereof may include a methylene group, an ethylene group, a trimethylene group, a tetramethylene group, and a hexamethylene group. Among them, an ethylene group or a trimethylene group is preferred, and a trimethylene group is particularly preferred.

The polyglutamic acid segment of the polymer compound of the present invention represented by general formula (1) has a structure in which glutamic acid units are polymerized in an α-amide bonded form. However, in such an amino acid polymerized structure, glutamic acid units that are polymerized in a γ-amide bonded form may also be included in some part. In regard to the polyglutamic acid segment, the glutamic acid units may be of L-type or D-type, or L-type and D-type forms may exist in mixture. The total number of the glutamic acid units in general formula (1) is represented by expression: (d+e), and is an integer from 6 to 60. Preferably, (d+e) is 8 to 40. Therefore, although the average molecular weight of the polyglutamic acid segment is dependent on the structures of the camptothecin derivative and the $R_3$ group that are bonded to each other as will be described below and the amount of linking groups, the average molecular weight is 0.6 kilodaltons to 15 kilodaltons, and preferably 0.8 kilodaltons to 10 kilodaltons.

The total number of glutamic acid units in the polyglutamic acid segment may be determined by a method for calculating the number of glutamic acid units by $^1$H-NMR, an amino acid analysis method, a method for acid-base titration of side chain carboxyl groups, or the like. It is preferable to employ the number of glutamic acid units determined from the amount of the side chain carboxyl groups by an acid-base titration method, using a polyglutamic acid segment before the camptothecin derivative and the $R_3$ group are bonded to a side chain.

The (C1-C6) acyl group which may have a substituent with regard to $R_2$ may be a linear, branched or cyclic (C1-C6) acyl group which may have a substituent. Examples thereof may include a formyl group, an acetyl group, a propionyl group, a butyryl group, and a valeryl group.

Regarding the substituent, the acyl group may include a hydroxyl group, a halogen atom, an amino group, an alkylamino group, a dialkylamino group, an alkoxy group, or an aryl group.

Preferred examples may include a formyl group, an acetyl group, a trichloroacetyl group, a trifluoroacetyl group, a propionyl group, a pivaloyl group, a benzylcarbonyl group, and a phenethylcarbonyl group. A linear, branched or cyclic (C1-C4) acyl group which may have a substituent is preferred, and an acetyl group, a trichloroacetyl group and a trifluoroacetyl group are preferred.

The (C1-C6) alkoxycarbonyl group which may have a substituent with regard to $R_2$ may be a linear, branched or cyclic (C1-C6) alkoxycarbonyl group which may have a substituent. Regarding the substituent, the alkoxycarbonyl group may include a hydroxyl group, a halogen atom, an amino group, an alkylamino group, a dialkylamino group, an alkoxy group, or an aryl group.

Preferred examples may include a methoxycarbonyl group, an ethoxycarbonyl group, a t-butoxycarbonyl group, a benzyloxycarbonyl group, and a 9-fluorenylmethyloxycarbonyl group.

$R_2$ is preferably a hydrogen atom or a linear, branched or cyclic (C1-C4) acyl group which may have a substituent. $R_2$ is particularly preferably a hydrogen atom, an acetyl group, a trichloroacetyl group, or a trifluoroacetyl group.

In regard to general formula (1), $R_3$ represents a hydroxyl group and/or $-N(R_6)CONH(R_7)$. That is, a glutamic acid unit in which a side chain carboxyl group is $R_3$ is a glutamic acid unit in which a side chain is unmodified, and/or a glutamic acid unit in which a urea derivative is bonded to a side chain.

$R_6$ and $R_7$ may be identical or different, and each represents a linear, branched or cyclic (C1-C8) alkyl group which may be substituted with a tertiary amino group. Examples of the (C1-C8) alkyl group for $R_6$ and $R_7$ may include a methyl group, an ethyl group, a n-propyl group, an isopropyl group, a n-butyl group, a t-butyl group, a cyclopropyl group, a cyclohexyl group, and a n-octyl group.

Examples of the linear, branched or cyclic (C1-C8) alkyl group which may be substituted with a tertiary amino group may include a 2-dimethylaminoethyl group and a 3-dimethylaminopropyl group.

Preferred examples of $R_6$ and $R_7$ may include an ethyl group, an isopropyl group, a cyclohexyl group, and a 3-dimethylaminopropyl group. More preferred examples may include a case in which $R_6$ and $R_7$ are both isopropyl groups, a case in which $R_6$ and $R_7$ are both cyclohexyl groups, and a case in which $R_6$ and $R_7$ are an ethyl group and a 3-dimethylaminopropyl group, respectively.

As will be described below, —N($R_6$)CONH($R_7$) with regard to $R_2$ is a glutamic acid side chain-modifying group that is produced as a side product by using a carbodiimide-based condensing agent when the block copolymer related to general formula (1) having a camptothecin derivative bonded thereto is synthesized. Therefore, these $R_6$ and $R_7$ become identical with the alkyl substituent of the carbodiimide-based condensing agent used therein. That is, when diisopropylcarbodiimide (DIPCI) is used as a carbodiimide condensing agent, $R_6$ and $R_7$ both are isopropyl groups. When 1-ethyl-3-(3-dimethylaminopropyl)carbodiimide hydrochloride (WSC) is used, $R_6$ and $R_7$ are mixed substituents of an ethyl group and a 3-dimethylaminopropyl group. In this case, there may exist a case where $R_3$ is an ethyl group and $R_7$ is a 3-dimethylaminopropyl group, and the case of vice versa, and a case where a —N($R_6$)CONH($R_7$) group in which these groups are co-present in one molecule.

In regard to general formula (1), $R_3$ may be a hydroxyl group. That is, the polyglutamic acid segment according to the present invention may have a free-form glutamic acid unit that is not bonded to any of the camptothecin derivative and the —N($R_6$)CONH($R_7$) group. The side chain carboxylic acid in the glutamic acid unit in which $R_3$ is a hydroxyl group may be in a free acid form; however, the side chain carboxylic acid may be in the form of a salt that may be used as a pharmaceutical product, and the side chain carboxylic acid in the form of an alkali metal salt or an alkaline earth metal salt is also included in the present invention. Examples of the alkali metal salt or alkaline earth metal salt may include lithium salt, sodium salt, potassium salt, magnesium salt, and calcium salt. In a case where the pharmaceutical preparation of the present invention is provided as an anticancer agent for parenteral administration, the block copolymer is solubilized in a pharmaceutically acceptable solubilizing liquid to prepare a solution. In that case, the embodiment of the free-form glutamic acid unit is dependent on the pH of the solution and the presence of salts of a buffer solution or the like, and an embodiment of any arbitrary glutamic acid salt may be adopted.

The block copolymer represented by general formula (1) comprises a camptothecin derivative bonded to a side chain carboxyl group of a polyglutamic acid segment via an ester bond. The camptothecin derivative has, at the 10-position, a hydroxyl group that is provided to the ester bond, and has a $R_4$ group at the 7-position, and a $R_5$ group at the 9-position. $R_4$ and $R_5$ may be a hydrogen atom; however, it is preferable that any one of $R_4$ and $R_5$ represents a substituent other than a hydrogen atom.

$R_4$ represents a hydrogen atom, a (C1-C6) alkyl group which may have a substituent, or a silyl group which may have a substituent.

The (C1-C6) alkyl group which may have a substituent with regard to $R_4$ may be a linear, branched or cyclic (C1-C6) alkyl group which may have a substituent. The substituent may include a hydroxyl group, a halogen atom, an amino group, an alkylamino group, a dialkylamino group, an alkoxy group, an aryl group, or the like. Examples thereof may include a methyl group, an ethyl group, a n-propyl group, an isopropyl group, a n-butyl group, a s-butyl group, a t-butyl group, and a benzyl group. A linear, branched or cyclic (C1-C4) alkyl group which may have a substituent is preferred, and an ethyl group is particularly preferred.

Examples of the silyl group which may have a substituent with regard to $R_4$ may include a trimethylsilyl group, a triethylsilyl group, a t-butyldimethylsilyl group, a triisopropylsilyl group, and a t-butyldiphenylsilyl group. A t-butyldimethylsilyl group is preferred.

$R_4$ is preferably a hydrogen atom or an unsubstituted (C1-C6) alkyl group. A hydrogen atom or an ethyl group is particularly preferred.

$R_5$ represents a hydrogen atom or a (C1-C6) alkyl group which may have a substituent.

The (C1-C6) alkyl group which may have a substituent with regard to $R_5$ may be a linear, branched or cyclic (C1-C6) alkyl group which may have a substituent. The substituent may include a hydroxyl group, a halogen atom, an amino group, an alkylamino group, a dialkylamino group, an alkoxy group, an aryl group, or the like. Examples thereof may include a methyl group, an ethyl group, a n-propyl group, an isopropyl group, a n-butyl group, a s-butyl group, a t-butyl group, a benzyl group, and a dimethylaminomethyl group.

$R_5$ is preferably a hydrogen atom or a (C1-C6) alkyl group having an amino group. A hydrogen atom or a dimethylaminomethyl group is particularly preferred.

The camptothecin derivative which provides a linking residue in general formula (1) is preferably 7-ethyl-10-hydroxycamptothecin and/or nogitecan (9-dimethylaminomethyl-10-hydroxycamptothecin). Such a camptothecin derivative is preferably 7-ethyl-10-hydroxycamptothecin in which $R_4$ is an ethyl group and $R_5$ is a hydrogen atom, residue of which is bonded via an ester bond. Alternatively, the camptothecin derivative is preferably nogitecan (9-dimethylaminomethyl-10-hydroxycamptothecin) in which $R_4$ is a hydrogen atom and $R_5$ is a dimethylaminomethyl group, residue of which is bonded via an ester bond. The camptothecin derivative is particularly preferably a linking residue to which 7-ethyl-10-hydroxycamptothecin in which $R_4$ is an ethyl group and $R_5$ is a hydrogen atom, is bonded via an ester bond.

The block copolymer represented by general formula (1) of the present invention preferably comprises a plurality of camptothecin derivatives. The camptothecin derivatives that are bonded to the same molecular chain of the block copolymer may be identical, or different types of derivatives may exist in a mixed state. However, it is preferable that the camptothecin derivatives bonded to the same molecular chain of the block copolymer are identical.

With regard to the polyglutamic acid segment in general formula (1), a glutamic acid unit to which a camptothecin derivative is bonded to a side chain carboxyl group, and a glutamic acid unit to which the $R_2$ group as defined above is bonded to a side chain carboxyl group exist each independently in a randomly arranged manner. Since the $R_3$ group may be a hydroxyl group and/or —N($R_6$)CONH($R_7$), the polyglutamic acid segment is a polyglutamic acid segment in which a glutamic acid unit having a camptothecin derivative bonded thereto, a glutamic acid unit having the —N($R_6$)CONH($R_7$) group bonded thereto, and a glutamic acid unit having a side chain that is a free carboxyl group or a salt thereof, each independently exist in a randomly arranged manner.

According to the present invention, the glutamic acid unit having a camptothecin derivative bonded thereto is an essential segment constitution. In general formula (1), the existing amount of the glutamic acid unit having a camptothecin derivative bonded thereto is represented by d, and the glutamic acid unit occupies 1% to 100% of the total degree of polymerization of glutamic acid segments. The existence ratio of d in the polyglutamic acid segment is preferably 20% to 70%. The amount of the camptothecin derivative bonded thereto determines the content of the active ingredient when the block copolymer is used as a pharmaceutical product, and has significant influence on the pharmacokinetics in the body after administration, thereby being involved in the manifestation of efficacy or side effects.

On the other hand, the glutamic acid unit having the above-defined $R_3$ group bonded thereto is an optional segment constitution. That is, the glutamic acid unit to which a camptothecin derivative is not bonded is the relevant $R_3$ group-bonded glutamic acid unit. In general formula (1), the existing amount of the $R_3$ group-bonded glutamic acid unit is represented by e, and the glutamic acid occupies 0% to 99% of the total degree of polymerization of the glutamic acid segments. The existence ratio of e in the polyglutamic acid segment is preferably 30% to 80%.

The $R_3$ group is a hydroxyl group and/or —$N(R_6)CONH(R_7)$. This —$N(R_7)CONH(R_7)$ group is an optional substituent, and for the glutamic acid unit to which a camptothecin derivative is not bonded, it is preferable that a hydroxyl group is a main substituent. With respect to the total degree of polymerization of glutamic acids in the polyglutamic acid segment (d+e), the existence ratio of the glutamic acid unit in which $R_3$ is a hydroxyl group is preferably 15% to 60%, and the existing ratio of the glutamic acid unit in which $R_3$ is —$N(R_6)CONH(R_7)$ is preferably 0% to 50%.

Meanwhile, the block copolymer represented by general formula (1) of the present invention has a physical property of forming associative aggregates in an aqueous solution. In order to obtain a stable associative aggregate-forming ability, the balance between the hydrophilicity of the polyethylene glycol segment and the hydrophobicity of the polyglutamic acid segment may be suitably attained. It is preferable to use a block copolymer in which t of the polyethylene glycol segment in general formula (1) is an integer from 90 to 340 and the total number of glutamic acid unit (d+e) is an integer from 8 to 40, and to use a block copolymer in which the existence ratio of d, which is the amount of existence of the glutamic acid unit having a camptothecin derivative bonded thereto, in the polyglutamic acid segment is 20% to 70%.

Next, the method for producing a block copolymer represented by general formula (1) according to the present invention will be explained by taking an example.

The block copolymer may be produced by bonding a camptothecin derivative having a hydroxyl group at the 10-position to "a block copolymer in which a polyethylene glycol segment and a free-form polyglutamic acid segment are linked", through an esterification reaction. Optionally, by subjecting a —$N(R_6)CONH(R_7)$ group as $R_3$ to a bonding reaction, the block copolymer having a camptothecin derivative bonded thereto according to the present invention may be produced. The methods for a bonding reaction between the camptothecin derivative having a hydroxyl group at the 10-position and the optional —$N(R_6)CONH(R_7)$ group are not particularly limited. A camptothecin derivative having a hydroxyl group at the 10-position may be first subjected to a bonding reaction, and then the —$N(R_6)CONH(R_7)$ group may be subjected to a bonding reaction; the processes may also be carried out in a reverse order; or the bonding reactions may also be carried out simultaneously.

Examples of the methods for constructing the "block copolymer in which a polyethylene glycol segment and a free-form polyglutamic acid segment are linked" may include a method of bonding a polyethylene glycol segment to a polyglutamic acid segment, and a method of sequentially polymerizing polyglutamic acids to a polyethylene glycol segment, and any of the methods may be employed.

The method for synthesizing a block copolymer represented by general formula (1) according to the present invention will be explained by taking an example in which the camptothecin derivative is 7-ethyl-10-hydroxycamptothecin, and the hydroxyl group at the 10-position of the camptothecin derivative and a carboxyl group of the glutamic acid segment of the block copolymer are bonded by an ester bond. Meanwhile, the relevant camptothecin derivative-bonded block copolymer may be produced by the method disclosed in WO 2004/039869. An outline of the production method described in this document will be given below.

The methods for synthesizing the "block copolymer in which a polyethylene glycol segment and a free-form polyglutamic acid segment are linked" include a method of constructing a polyglutamic acid structural moiety at one terminal of the polyethylene glycol segment, by sequentially reacting N-carbonyl glutamic acid anhydride with a polyethylene glycol compound having one terminal modified with an alkoxy group and the other terminal modified with an amino group. In this case, regarding the N-carbonyl glutamic acid anhydride, it is preferable that the carboxyl group in a side chain of glutamic acid is a glutamic acid derivative modified with an appropriate carboxylic acid protective group. The carboxylic acid protective group is not particularly limited; however, an ester protective group is preferred.

More specifically, a method of producing a block copolymer having a polyethylene glycol segment and a polyglutamic acid segment through sequential polymerization, by sequentially reacting γ-benzyl-N-carbonyl glutamic acid anhydride with a polyethylene glycol having one terminal modified with a methoxy group and the other terminal modified with an amino group, may be employed. At this time, the degree of polymerization of glutamic acid in the polyglutamic acid segment may be controlled by adjusting the equivalent of the γ-benzyl-N-carbonyl glutamic anhydride to be used.

Subsequently, benzyl groups of the polyglutamic acid segment are deprotected by an appropriate method to produce the "block copolymer in which a polyethylene glycol segment and a polyglutamic acid segment are linked". Regarding a deprotection reaction for benzyl groups, a hydrolysis reaction under alkali conditions and a hydrogenation reduction reaction may be employed.

Next, 7-ethyl-10-hydroxycamptothecin is subjected to a condensation reaction with the "block copolymer in which a polyethylene glycol segment and a free-form polyglutamic acid segment are linked", in the presence of a carbodiimide condensing agent. By using this method, 7-ethyl-10-hydroxycamptothecin and the —$N(R_6)CONH(R_7)$ group may be simultaneously bonded to the block copolymer, and therefore, this method of reaction is advantageous. Meanwhile, in regard to the condensation reaction, the amount of bonding of the camptothecin derivative may be controlled by adjusting the equivalent amount of 7-ethyl-10-hydroxycamptothecin to be used. Furthermore, the amount of introduction of the —$N(R_6)CONH(R_7)$ group may be controlled by adjusting the use equivalent amount of the carbodiimide condensing agent.

Excluding the glutamic acid units having the camptothecin derivative and the —$N(R_6)CONH(R_7)$ group bonded thereto, the remaining glutamic acid units in which side chain carboxyl groups are not chemically modified constitute the glutamic acid units in which $R_3$ is a hydroxyl group. The amount of the glutamic acid units in which $R_3$ is a hydroxyl group may be controlled by means of the equivalent amounts of the camptothecin derivative and the carbodiimide condensing agent to be used.

Meanwhile, regarding the carbodiimide condensing agent used herein, any condensing agent may be used without any particular limitations as long as the agent is capable of ester bonding the camptothecin derivative to a side chain carboxyl group of a glutamic acid unit. Preferred examples may include dicyclohexylcarbodiimide (DCC), diisopropylcarbodiimide (DIPCI), and 1-ethyl-3-(3-dimethylaminopropyl) carbodiimide hydrochloride (WSC). At the time of the condensation reaction, a reaction auxiliary agent such as N,N-dimethylaminopyridine (DMAP) may also be used. Meanwhile, when DCC is used as a carbodiimide condensing agent, $R_6$ and $R_7$ are cyclohexyl groups; when DIPCI is used, $R_6$ and $R_7$ are isopropyl groups; and when WSC is used, $R_6$ and $R_7$ are a mixture of an ethyl group and a 3-dimethylaminopropyl group.

When an appropriate amount of 7-ethyl-10-hydroxycamptothecin and an appropriate amount of a —N($R_6$)CONH ($R_7$) group as an optional substituent for $R_3$ are bonded, through the reaction described above, to a glutamic acid side chain of the "block copolymer in which a polyethylene glycol segment and a free-form polyglutamic acid segment are linked", and then a purification process is carried out as appropriate, the block copolymer having a camptothecin derivative bonded thereto according to the present invention may be synthesized. In the purification process, it is preferable to produce a side chain hydroxyl group-containing form of polyglutamic acid into a free acid form, while simultaneously removing residual amine components, by means of a cation exchange resin or the like.

The block copolymer having a camptothecin derivative bonded thereto as represented by general formula (1) has a performance of slowly releasing the camptothecin derivative in a phosphate buffer saline (PBS) solution and continuously releasing the camptothecin derivative. For example, when the camptothecin derivative is 7-ethyl-10-hydroxycamptothecin and is ester-bonded via the hydroxyl group at the 10-position, the block copolymer has a physical property of slowly releasing 7-ethyl-10-hydroxycamptothecin when administered into the body. Low molecular weight drugs that are generally used for clinical purposes achieve the maximum blood concentrations of the drugs immediately after being administered, and then are relatively rapidly excreted from the body. In contrast, the camptothecin derivative-bonded block copolymer is a preparation characterized in that, due to the slow elimination of 7-ethyl-10-hydroxycamptothecin as an active ingredient, the block copolymer exhibits a persistent blood concentration profile without excessively increasing the blood concentration of the active ingredient in the blood after administration.

Furthermore, in the camptothecin derivative-bonded block copolymer, the polyethylene glycol segment in the block copolymer is hydrophilic. On the other hand, the polyglutamic acid segment includes the hydrophilic camptothecin derivative. Thus, the camptothecin derivative-bonded block copolymer has associative properties based on a hydrophobic interaction between the polyglutamic acid segments in an aqueous solution. Therefore, the block copolymer in an aqueous solution forms core-shell type micellar associates, in which hydrophobic polyglutamic acid segments form a core as a result of association and aggregation, while hydrophilic polyethylene glycol segments cover the circumference of the core to form an outer shell, thereby forming a shell layer.

With regard to the micellar associates, the formation of association may be confirmed by measuring the light scattering intensity using laser light or the like, and thus, associate-forming properties may be evaluated based on the light scattering intensity value. For example, the light scattering intensity may be directly used as a physical property value for the associative aggregate-forming properties. With regard to an aqueous solution of the block copolymer, for example, an aqueous solution of the block copolymer at a concentration of 0.01 to 100 mg/mL exhibits several thousand cps to several hundred thousand cps as a light scattering intensity value, and it is acknowledged that associative aggregates are formed. Furthermore, the total molecular weight of the associative aggregates may be estimated from the light scattering intensity based on high molecular weight standards of polyethylene glycol or the like. The block copolymer forms associative aggregates in an aqueous solution, and it may be calculated from the results of a light scattering intensity analysis that those associative aggregates have a total molecular weight of several millions or more. Therefore, it is contemplated that the micellar associates are formed when a plurality of molecules of the block copolymer, such as several dozen molecules to several hundred molecules, associate together. According to the present invention, the apparent molecular weight calculated by a light scattering intensity analysis of the associative aggregates formed in an aqueous solution on the basis of polyethylene glycol standards, is referred to as the total molecular weight of the associates.

Furthermore, an aqueous solution of the block copolymer has a physical property of forming nanoparticulate bodies having a particle size of several nanometers to several hundred nanometers according to a particle size analysis based on a dynamic light scattering analysis.

When administered into the body, the block copolymer that forms nanoparticles as associative aggregates in an aqueous solution is distributed in the body in the form of the above-mentioned associative nanoparticles in blood. A high molecular weight compound or a nanoparticulate object has a significantly different pharmacokinetic behavior or tissue distribution in the body, compared to low molecular weight drugs that are conventionally used. Therefore, it is known that the retention in the body or the distribution in the tissue of the camptothecin derivative-bonded block copolymer capable of forming associative nanoparticles is determined depending on the associate's molecular weight or the particle size of the nanoparticles, and the block copolymer is retained and distributed particularly in tumor tissues. From this point of view, the camptothecin derivative-bonded block copolymer is an antitumor preparation completely different from conventional low molecular weight camptothecin preparations in that they have different efficacy-manifesting characteristics and side effect-manifesting characteristics from each other, and thus is capable of providing a new therapeutic method in clinical use of camptothecin derivatives. Therefore, since the relevant block copolymer is in the form of nanoparticles which are formed by particular associative properties and are controlled to have a desired associate molecular weight (total molecular weight) and a desired particle size, it is important to achieve pharmacokinetics and a distribution in the tissue that are preferable as an antitumor agent, and the formation of nanoparticles having a desired associate molecular weight and a desirable particle size may be listed as an important product quality control item for performance demonstration.

The present invention relates to a pharmaceutical preparation containing the camptothecin derivative-bonded block copolymer as an active ingredient, that is, an invention related to a pharmaceutical unit preparation obtained by filling the block copolymer into a predetermined dosage form at an arbitrary content.

When the camptothecin derivative-bonded block copolymer is used as a pharmaceutical product, it is preferable to use the block copolymer as a pharmaceutical preparation in an appropriate dosage form. The pharmaceutical preparation which is conventionally used in dosage forms such as an injectable preparation, an infusion preparation, a tablet preparation, a capsule preparation, and a powder preparation, may be used. That is, the present invention is a pharmaceutical unit preparation that contains the block copolymer in a predetermined amount and also contains optional additives in these dosage forms.

When producing a pharmaceutical preparation, usually, a preparation formulation durable against long-term storage is examined by using pharmaceutically acceptable additives, in view of the chemical stability of the active ingredient. In the case of a pharmaceutical preparation comprising the camptothecin derivative-bonded block copolymer of the present invention as an active ingredient, since the property of forming nanoparticles when produced into an aqueous solution is an important product quality control item, it is necessary to consider the stability of the nanoparticle-forming properties as well when formulating a preparation.

The nanoparticle-forming properties of a pharmaceutical preparation comprising the camptothecin derivative-bonded block copolymer of the present invention as an active ingredient may be evaluated based on the associate-forming properties observed by a light scattering intensity analysis. For example, the associate-forming properties may be evaluated using a measuring instrument capable of measuring the laser light scattering intensity, by taking the light scattering intensity as an index.

Specifically, an aqueous solution of the pharmaceutical preparation comprising a camptothecin derivative-bonded block copolymer may be used as a measurement sample, and the measured value of the light scattering intensity of the sample may be used as the physical property value of the associate-forming properties. Furthermore, the associate molecular weight or particle size calculated from the light scattering intensity may also be used as an index for the associate-forming properties.

Regarding the measuring instrument for a light scattering intensity analysis, for example, measurement may be made using a dynamic light scattering photometer manufactured by Otsuka Electronics Co., Ltd., DLS-8000DL, or NICOMP Model 380 ZLS-S manufactured by Particle Sizing Systems, LLC.

It is desirable that the camptothecin derivative-bonded block copolymer of the present invention is in the form of a preparation whose associate-forming properties are maintained stably during storage. Specifically, it is desirable that the block copolymer is in the form of a pharmaceutical preparation for which stability is secured for at least 2 years to 3 years under refrigeration. Alternatively, it is desirable that the block copolymer is in the form of a pharmaceutical preparation for which stability is secured for at least 3 years under refrigeration.

Regarding an evaluation method for the stability of a pharmaceutical preparation comprising the relevant camptothecin derivative-bonded block copolymer as an active ingredient, the change ratio for the associate-forming properties when the pharmaceutical preparation is stored at 40° C. for one week under light-blocked conditions may be employed as an index. Regarding the evaluation method, the change ratio for the associate formation may be evaluated by comparing the value of the light scattering intensity obtained by a light scattering intensity analysis, or the value of the associate molecular weight or the particle size calculated from this light scattering intensity, with the initial value of the corresponding property obtained before storage. In regard to the relevant pharmaceutical preparation comprising the camptothecin derivative-bonded block copolymer as an active ingredient, when the pharmaceutical preparation is stored at 40° C. for one week under light-blocked conditions, the change ratio for the associate-forming properties determined by taking the associate molecular weight (total molecular weight) as an index is 50% or less. That is, when the associate-forming properties are significantly deteriorated during the storage of the preparation, and the original associative nanoparticles which were initially formed may not be formed, there occurs a problem that the effectiveness of the camptothecin derivative-bonded block copolymer is deteriorated. Therefore, it is desirable that the pharmaceutical preparation is a preparation which does not undergo deterioration in the associate-forming properties under storage conditions. In regard to the test method, it is preferable that the change ratio for the associate formation determined by taking the associate molecular weight as an index is 30% or less. Meanwhile, the change ratio of the associate molecular weight is a value expressed as an absolute value, of the increase or decrease ratio of the change ratio value obtainable after storing at 40° C. for one week with respect to the initial value.

Furthermore, for the evaluation of the change ratio for the associate formation obtained by taking the particle size of the associative nanoparticles as an index, when the pharmaceutical preparation has stored at 40° C. for one week under light-blocked conditions, the change ratio of the particle size needs to be 0.25 times or more and 5 times or less the original particle size. When the change ratio for the associate formation obtained by taking the particle size as an index, it is preferable that the change ratio is 0.5 times or more and 2.5 times or less the original particle size. Meanwhile, the change ratio of the particle size of the associative nanoparticles is a value expressed as a ratio of the value obtained after storage at 40° C. for one week with respect to the initial value.

Furthermore, the change ratio of the amount of scattered light, which represents the light scattering intensity, is a value expressed as a ratio of the value obtained after storage at 40° C. for one week to two weeks with respect to the initial value.

In order to produce a pharmaceutical preparation having a small change ratio for the associates and having excellent preparation storage stability as a pharmaceutical preparation comprising the camptothecin derivative-bonded block copolymer of the present invention as an active ingredient, when the pharmaceutical preparation is made into an aqueous solution comprising the camptothecin derivative at a concentration of 1 mg/mL, it is necessary to set the pH of the aqueous solution in the range of 2.4 to 7.0. This pH range needs to be set at the preparation of a solution of the pharmaceutical preparation comprising the camptothecin derivative-bonded block copolymer as an active ingredient. In the case of a solid-state preparation such as a freeze-dried preparation, for example, when the pharmaceutical preparation is reconstituted into an aqueous solution, the pH of the aqueous solution needs to be in the range of 2.4 to 7.0. In regard to the camptothecin derivative-bonded block copolymer, since it is necessary to consider chemical stability in a low pH region, which is an acidic region, or in a neutral-alkaline region, it is preferable to adjust the pH to the range of 3.0 to 7.0. More preferably, when the pharmaceutical preparation is made into an aqueous solution containing the camptothecin derivative at a concentration of 1 mg/mL, the pH of the aqueous solution has been adjusted to the range of 3.0 to 6.5.

When the pH of the aqueous solution is lower than 2.4, it is observed that the associate molecular weight of the block copolymer is markedly decreased compared to the original molecular weight, and the associate-forming ability of the block copolymer is extremely deteriorated. Furthermore, on the occasion of measuring the particle size of the block copolymer, the particle size of the associative aggregates in an aqueous solution of the block copolymer becomes as large as several hundred nanometers even at the initial time, and when it is stored at 40° C. for one week, it is observed that the particle size is further enlarged, and a significant change occurs in the associate-forming properties. At a low pH, which is in an acidic range, there is a risk that the chemical stability of the block copolymer may be deteriorated; therefore, it is preferable to adjust the pH to 3.0 or higher.

On the other hand, when the pH of the aqueous solution is higher than 7.0, it is observed that the associate molecular weight of the block copolymer is smaller than the original molecular weight, and the associate-forming properties are significantly deteriorated. Furthermore, when it is stored at 40° C. for one week, the associate-forming ability of the block copolymer is extremely deteriorated, and therefore, it is not preferable. On the occasion of measuring the particle size of the block copolymer, it is observed that the particle size of the associative aggregates in an aqueous solution of the block copolymer is enlarged, and a significant change occurs in the associate-forming properties, when it is stored at 40° C. for one week. In a neutral to alkaline range, there is a risk that the chemical stability of the block copolymer may be deteriorated, and thus it is preferable that the pH is set to 6.5 or lower.

When the associate-forming ability of the block copolymer is deteriorated, the existence of the block copolymer that has been dissociated from the associate-formed bodies is recognized. By size exclusion chromatography (SEC), for example, associate-formed bodies of the block copolymer may be separated from the molecular species of the block copolymer that has been dissociated from these associate-formed bodies. Thus, a tendency is observed that the existence ratio of the associate-formed bodies is decreased, while the existence ratio of the block copolymer that has been dissociated from the associate-formed bodies increases.

In the case of a pharmaceutical preparation in which the pH of the aqueous solution is not in the range of 2.4 to 7.0, a tendency for significant decrease in the associate-forming ability of the block copolymer is observed by the SEC method.

Furthermore, in the case of a pharmaceutical preparation in which the pH of the aqueous solution is not in the range of 2.4 to 7.0, the chemical stability of the relevant active ingredient is deteriorated, and analogous substances including low molecular weight compounds are increased, which is not preferable.

From this point of view, in order to secure the stability of the associate-forming properties of the block copolymer, it is important to control the pH of the pharmaceutical preparation. Preferably, in the case where the pharmaceutical preparation is made into an aqueous solution containing the camptothecin derivative at a concentration of 1 mg/mL, the pH of the aqueous solution is 2.4 to 7.0. Particularly preferably, the pH of the aqueous solution is 3.0 to 7.0. When chemical stability during long-term storage is considered, the pH of the aqueous solution may be set in the range of 3.0 to 6.5, particularly preferably in the range of 3.0 to 5.0.

When the pharmaceutical preparation of the present invention is made into an aqueous solution containing the camptothecin derivative at a concentration of 1 mg/mL, it is necessary to adjust the pH of the aqueous solution to the range of 2.4 to 7.0, preferably to the range of 3.0 to 7.0, and particularly preferably to the range of 3.0 to 6.5. For this pH adjustment, the pH may be adjusted using a pH adjusting agent as an additive. Preferred is a pharmaceutical preparation comprising the pH adjusting agent and having a pH adjusted to 2.4 to 7.0, preferably to 3.0 to 7.0, more preferably to 3.0 to 6.5, and particularly preferably adjusted to 3.0 to 5.0, when the pharmaceutical preparation is made into an aqueous solution. That is, a pH adjusting agent that is capable of adjusting to acidity may be used for an aqueous solution of the pharmaceutical preparation, and as a pH adjusting agent, an acidic compound is used. Furthermore, since the camptothecin derivative-bonded block copolymer has free carboxyl groups, when the pH is adjusted to 4.0 to 7.0, and preferably to 4.5 to 7.0, an alkaline compound is used. Also, the acidic compound and the alkaline compound described above may also be used as a mixture, that is, a so-called buffering agent.

As the pH adjusting agent used for the present invention, any acids that may be used as a pharmaceutical additive may be used without any particular limitations, and examples thereof may include hydrochloric acid, sulfuric acid, phosphoric acid, citric acid, tartaric acid, malic acid, mesylic acid, tosylic acid, and besylic acid. A buffering agent including such an acidic additive as a main component and including an alkali metal salt, an alkaline earth metal salt, or an ammonium salt in addition to the acidic additive, may also be used. Preferably, hydrochloric acid, phosphoric acid, citric acid, or tartaric acid is used, and it is preferable to use the acidic compound in an appropriate amount of addition such that the pH of the pharmaceutical preparation as an aqueous solution is 2.4 to 7.0, preferably 3.0 to 7.0, more preferably 3.0 to 6.5, and particularly preferably 3.0 to 5.0. More preferred is a pharmaceutical preparation produced using hydrochloric acid, phosphoric acid, citric acid or tartaric acid as a pH adjusting agent, in which the pH of the aqueous solution of the pharmaceutical preparation has been adjusted to 3.0 to 6.0, and particularly preferred is a pharmaceutical preparation having the pH adjusted to 3.0 to 5.0.

Furthermore, regarding the alkaline compound used as a pH adjusting agent, any alkaline compound that may be used as a pharmaceutical additive may be used without any particular limitations, and examples thereof may include hydroxides such as sodium hydroxide and potassium hydroxide; carbonates and hydrogen carbonates such as sodium carbonate, potassium carbonate, sodium hydrogen carbonate, and potassium hydrogen carbonate; phosphates such as sodium dihydrogen phosphate, disodium hydrogen phosphate, and sodium phosphate; and organic acid salts such as sodium acetate, sodium tartrate, sodium citrate, and sodium malate. Preferred examples may include sodium hydrogen carbonate and disodium hydrogen phosphate. It is preferable to use the alkaline compound in an appropriate amount so that the pH of the aqueous solution of the pharmaceutical preparation is set to 3.0 to 6.5.

Furthermore, the camptothecin derivative-bonded block copolymer represented by general formula (1), which is the pharmaceutically active ingredient related to the present invention, may have a hydroxyl group for $R_3$, and may include a glutamic acid unit in which a side chain is a free carboxylic acid. Therefore, the pH of the aqueous solution may be adjusted to 2.4 to 7.0, preferably 3.0 to 7.0, more preferably to 3.0 to 6.5, and particularly preferably to 3.0 to 5.0, only using the active ingredient.

That is, it is preferable that the block copolymer used as an active ingredient comprises as an essential component a glutamic acid unit wherein $R_3$ is a hydroxyl group, and that, when the block copolymer is produced into an aqueous solution containing the camptothecin derivative at a concentration of 1 mg/mL, the pH of the aqueous solution may be adjusted to 3.0 to 6.5, preferably 3.0 to 6.0, and particularly preferably 3.0 to 5.0.

By using the block copolymer exhibiting acidity as described above as an active ingredient, a pharmaceutical preparation with secured associate-forming properties may be produced, particularly without using a pH adjusting agent as an additive.

That is, the block copolymer of the present invention is preferably a block copolymer in which $R_3$ of the camptothecin derivative-bonded block copolymer represented by general formula (1) includes a hydroxyl group as an essential component, and the content of the glutamic acid unit in which $R_3$ is a hydroxyl group is 15% to 60% with respect to the total degree of polymerization of the polyglutamic acid segment in the block copolymer. In this case, the camptothecin derivative-bonded block copolymer represented by general formula (1) is preferably a block copolymer in which the content of the glutamic acid unit having the camptothecin derivative bonded thereto is 20% to 70%, and the content of the glutamic acid in which $R_3$ is the —$N(R_6)CONH(R_7)$ group occupies 0% to 50%. In this case, when $R_3$ is a hydroxyl group, the glutamic acid unit is a glutamic acid unit in which the side chain carboxyl group is a free-form carboxyl group. This side chain carboxylic acid is in a free acid form but may be in a pharmaceutically acceptable salt form, and embodiments in the form of an alkali metal salt form or an alkaline earth metal salt form are also included in the present invention. Examples of the alkali metal salt or the alkaline earth metal salt may include a lithium salt, a sodium salt, a potassium salt, a magnesium salt, and a calcium salt. In that case, the pharmaceutical preparation of the present invention may be produced using the pH adjusting agent described above, and when the pharmaceutical preparation is made into an aqueous solution containing the camptothecin derivative at a concentration of 1 mg/mL, adjusting the pH of the aqueous solution to 3.0 to 6.5, preferably adjusting the pH to 3.0 to 6.0, and particularly preferably adjusting the pH to 3.0 to 5.0.

The present invention is preferably a pharmaceutical preparation wherein the camptothecin derivative-bonded block copolymer represented by general formula (1) uses a pharmaceutically active ingredient which, when the pharmaceutical preparation is made into an aqueous solution containing the camptothecin derivative at a concentration of 1 mg/mL, has a pH of the aqueous solution of 3.0 to 6.5, and wherein the pH of the aqueous solution is adjusted to 2.4 to 7.0 by adding a pH adjusting agent to this pharmaceutically active ingredient. More preferably, a pharmaceutical composition in which the pH of the aqueous solution is adjusted to 3.0 to 7.0, and even more preferred is a pharmaceutical composition in which the pH is adjusted to 3.0 to 6.5. Particularly preferred is a pharmaceutical preparation wherein the camptothecin derivative-boned block copolymer represented by general formula (1) uses a pharmaceutically active ingredient which, when the pharmaceutical preparation is produced into an aqueous solution containing the camptothecin derivative at a concentration of 1 mg/mL, has a pH of the aqueous solution of 3.0 to 6.0, and wherein the pH of the aqueous solution has been adjusted to 3.0 to 6.0 using a pH adjusting agent, is particularly preferred.

The pharmaceutical preparation of the present invention is preferably a preparation for injection or infusion that is administered into the blood vessels, and is preferably an injectable preparation that may be intravenously administered. The dosage form is preferably a freeze-dried preparation, an injectable liquid preparation that may be made into an injectable solution by diluting at the time of use, or a diluted solution preparation that may be directly administered.

That is, when administered as a pharmaceutical product, the pharmaceutical preparation is usually used as a solution of the pharmaceutical preparation prepared using water, physiological saline, a 5% aqueous solution of glucose or mannitol, a water-soluble organic solvent (for example, a single solvent such as glycerol, ethanol, dimethyl sulfoxide, N-methylpyrrolidone, polyethylene glycol, or Cremophor, or a mixed solvent thereof), or the like.

When the chemical stability and associate-forming properties' stability of the camptothecin derivative-bonded block copolymer are considered, the pharmaceutical preparation is preferably a freeze-dried preparation.

The pharmaceutical preparation of the present invention may comprise pharmaceutically acceptable additives that are conventionally used. Examples of the additives to be used may include a binder, a lubricating agent, a disintegrant, a solvent, an excipient, a solubilizing agent, a dispersant, a stabilizer, a suspending agent, a preservative, a soothing agent, a colorant, and a fragrance.

Regarding the additives for the pharmaceutical preparation of the present invention, it is preferable to use sugars, polyols, polyethylene glycols, amino acids, inorganic salts and the like.

The sugars used for a pharmaceutical preparation generally function as excipients, and the sugars according to the present invention are used also as excipients.

Examples of the sugars may include arabinose, isomaltose, galactosamine, galactose, xylose, glucosamine, glucose, gentiobiose, kojibiose, sucrose, cellobiose, sophorose, thioglucose, turanose, deoxyribose, trehalose, nigerose, palatinose, fucose, fructose, maltose, mannose, melibiose, lactose, rhamnose, and laminaribiose.

Examples of the polyols may include xylitol, sorbitol, maltitol, mannitol, and meglumine.

Examples of the polyethylene glycols may include polyethylene glycol 300, polyethylene glycol 400, polyethylene glycol 600, and polyethylene glycol 4000.

Examples of the amino acids may include aspartic acid, arginine, glycine, glutamic acid, serine, histidine, and lysine hydrochloride.

Examples of the inorganic salts may include calcium chloride, sodium chloride, calcium oxide, and magnesium sulfate. More preferably, it is preferable to use inositol, glucose, trehalose, fructose, maltose, mannitol, or lactose.

The additives to be used may not be particularly limited, as long as the additives have the purity suitable for pharmaceutical preparations. They may be used alone, or may be used as mixtures thereof.

In regard to the pharmaceutical preparation of the present invention, it is preferable to use the additives in an amount of 0.5 to 50 times the mass of the block copolymer. More preferably, it is desirable to use the additives in an amount of 1 to 30 times the mass of the block copolymer. It is particularly preferable to use the additives in an amount of 3 to 25 times the mass of the block copolymer.

The pharmaceutical preparation of the present invention is preferably a preparation that is intravascularly administered, such as an injectable preparation or a drip infusion, and preferably a dosage form such as a freeze-dried preparation or an injectable liquid preparation.

In the case of producing a freeze-dried preparation, an aqueous solution is produced using the camptothecin derivative-bonded block copolymer as a pharmaceutically active ingredient, together with optional preparation additives to produce a medicinal liquid by adjusting the pH of the aqueous solution. A freeze-dried preparation is obtained by, preferably after filtration and sterilization of the medicinal liquid, dispensing it into a vial and freeze-drying it. For the adjustment of pH, a pH adjusting agent may be used, or pH adjustment may be carried out with the active ingredient itself, using a camptothecin derivative-bonded block copolymer including, as an active ingredient, a glutamic acid unit in which a side chain is a free-form carboxylic acid.

On the other hand, in the case of producing an injectable liquid preparation, an aqueous solution is prepared using the block copolymer together with optional preparation additives. Subsequently, the aqueous solution is made into a medicinal liquid having its pH adjusted, and an injectable liquid preparation may be produced by, preferably after filtration and sterilization of the medicinal liquid, dispensing the resultant liquid into a preparation container. For the adjustment of pH, a pH adjusting agent may be used, or pH adjustment may be carried out with the active ingredient itself.

The pharmaceutical preparation of the present invention has an excellent stability for the associate-forming rate, and the change ratio of the particle size analyzed with the aqueous solution is small even if the pharmaceutical preparation is stored at 40° C. for one week under light-blocked conditions.

A pharmaceutical preparation comprising the camptothecin derivative-bonded block copolymer of the present invention as an active ingredient may be utilized as a pharmaceutical product comprising a camptothecin derivative as an active ingredient. It is particularly preferable to use the pharmaceutical preparation as an antitumor agent for cancer chemotherapy.

The application of the pharmaceutical preparation of the present invention is not particularly limited as long as the lesions are cancers or tumors on which the camptothecin derivative provides a therapeutic effect. Specific examples may include small cell lung cancer, non-small cell lung cancer, cervical cancer, ovarian cancer, gastric cancer, colorectal cancer, breast cancer, squamous cell carcinoma, malignant lymphoma, infant malignant solid tumor, pancreatic cancer, and multiple myeloma.

The dosage of the pharmaceutical preparation of the present invention may definitely vary depending on the gender, age, physiological condition and pathologic condition of the patient, or the like; however, the pharmaceutical preparation is usually parenterally administered in an amount of 0.01 to 500 mg/m$^2$ (body surface area), and preferably 0.1 to 250 mg/m$^2$, in terms of the camptothecin derivative, per day for an adult. It is preferable that administration by injection is performed at the vein, artery, lesions (areas of the tumor), or the like.

EXAMPLES

Synthesis Example 1

Synthesis of 7-ethyl-10-hydroxycamptothecin-bonded block copolymer (Compound 1), in which in general formula (1), $R_1$=methyl group, $R_2$=acetyl group, A=trimethylene group, $R_6$=$R_7$=isopropyl group, d+e=24, t=273, proportion of d with respect to d+e is 44%, proportion of e is 56% (the percentage content of glutamic acid unit with hydroxyl group for $R_3$ is 30%, and percentage content of glutamic acid unit with —N($R_6$)CONH($R_7$) for $R_3$ is 26%).

Compound 1 was synthesized based on the description of WO 2004/39869. That is, a methoxypolyethylene glycol-polyglutamic acid block copolymer (a block copolymer having a molecular weight of 12 kilodaltons, including a methoxypolyethylene glycol structural moiety with a methyl group at one terminal and an aminopropyl group at the other terminal, and a polyglutamic acid structural moiety having the N-terminal modified with an acetyl group and having a polymerization number of 24, with the linking group being a trimethylene group) was reacted with 7-ethyl-10-hydroxycamptothecin (EHC) using diisopropylcarbodiimide (DIPCI) and N,N-dimethylaminopyridine (DMAP). Subsequently, the reaction product was treated with an ion exchange resin (DOWEX 50 (H$^+$) manufactured by Dow Chemical Company) and was freeze-dried. Thus, Compound 1 was obtained.

Compound 1 thus obtained was subjected to hydrolysis for 10 minutes at room temperatures using an aqueous solution of sodium hydroxide, and then liberated EHC was quantitatively analyzed by a HPLC method to determine the EHC content. The EHC content was 19.50% by mass.

Synthesis Example 2

Compound 2 was obtained by a method equivalent to Synthesis Example 1.

For Compound 2 thus obtained, liberated EHC was quantitatively analyzed by a HPLC method similarly to Synthesis Example 1 to determine the EHC content. The EHC content was 19.76% by mass.

Example 1

3 mL of a solution comprising Compound 1 at a concentration of 1 mg/mL in terms of the EHC content was prepared using water for injection. This was introduced into a glass vial and freeze-dried. Subsequently, the glass vial was tightly sealed with a rubber stopper. This freeze-dried preparation was designated as Example 1.

When the freeze-dried preparation thus obtained was redissolved in 3 mL of water for injection, the pH was 4.7. In all of the following Examples and Test Examples, pH measurement was carried out at room temperature (25° C.).

Example 2

3 mL of a solution of Compound 1 was prepared in the same manner as in Example 1. This solution was adjusted to pH 3.0 using phosphoric acid, and this was freeze-dried. This freeze-dried preparation was designated as Example 2.

When the freeze-dried preparation thus obtained was redissolved in 3 mL of water for injection, the pH was 3.0.

Example 3

3 mL of a solution of Compound 1 was prepared in the same manner as in Example 1. This solution was adjusted to pH 6.0 using sodium hydrogen carbonate, and this was freeze-dried. This freeze-dried preparation was designated as Example 3.

When the freeze-dried preparation thus obtained was redissolved in 3 mL of water for injection, the pH was 6.5.

Example 4

3 mL of a solution of Compound 2 was prepared in the same manner as in Example 1. This solution was adjusted to pH 3.0 using phosphoric acid, and this was freeze-dried. This freeze-dried preparation was designated as Example 4.

When the freeze-dried preparation thus obtained was redissolved in 3 mL of water for injection, the pH was 2.9.

Example 5

3 mL of a solution of Compound 2 was prepared in the same manner as in Example 1. This solution was adjusted to pH 3.5 using phosphoric acid, and this was freeze-dried. This freeze-dried preparation was designated as Example 3.

When the freeze-dried preparation thus obtained was redissolved in 3 mL of water for injection, the pH was 3.5.

Example 6

3 mL of a solution of Compound 2 was prepared in the same manner as in Example 1. This solution was adjusted to pH 4.5 using phosphoric acid, and this was freeze-dried. This freeze-dried preparation was designated as Example 6.

When the freeze-dried preparation thus obtained was redissolved in 3 mL of water for injection, the pH was 4.5.

Example 7

3 mL of a solution of Compound 2 was prepared in the same manner as in Example 1. This solution was adjusted to pH 6.0 using sodium hydrogen carbonate, and this was freeze-dried. This freeze-dried preparation was designated as Example 7.

When the freeze-dried preparation thus obtained was redissolved in 3 mL of water for injection, the pH was 6.9.

Example 8

3 mL of a solution prepared by dissolving Compound 2 and maltose using water for injection, and adjusting the concentration to 1 mg/mL in terms of the EHC content and a concentration of 5 mg/mL for maltose, was adjusted to pH 4.0 using phosphoric acid. This was introduced into a glass vial and freeze-dried. Subsequently, the glass vial was tightly sealed with a rubber stopper. This freeze-dried preparation was designated as Example 8.

When the freeze-dried preparation thus obtained was redissolved in 3 mL of water for injection, the pH was 4.2.

Example 9

3 mL of a solution prepared by dissolving Compound 2 and lactose using water for injection, and adjusting the concentration to 1 mg/mL in terms of the EHC content and a concentration of 5 mg/mL for lactose, was adjusted to pH 4.0 using phosphoric acid. This was introduced into a glass vial and freeze-dried. Subsequently, the glass vial was tightly sealed with a rubber stopper. This freeze-dried preparation was designated as Example 9.

When the freeze-dried preparation thus obtained was redissolved in 3 mL of water for injection, the pH was 4.2.

Example 10

3 mL of a solution of Compound 2 was prepared in the same manner as in Example 1. This solution was adjusted to pH 3.2 using citric acid, and this was freeze-dried. This freeze-dried preparation was designated as Example 10.

When the freeze-dried preparation thus obtained was redissolved in 3 mL of water for injection, the pH was 3.2.

Example 11

3 mL of a solution of Compound 2 was prepared in the same manner as in Example 1. This solution was adjusted to pH 4.0 using citric acid, and this was freeze-dried. This freeze-dried preparation was designated as Example 11.

When the freeze-dried preparation thus obtained was redissolved in 3 mL of water for injection, the pH was 4.2.

Example 12

3 mL of a solution of Compound 2 was prepared in the same manner as in Example 1. This solution was adjusted to pH 5.0 using disodium hydrogen phosphate, and this was freeze-dried. This freeze-dried preparation was designated as Example 12.

When the freeze-dried preparation thus obtained was redissolved in 3 mL of water for injection, the pH was 5.0.

Example 13

3 mL of a solution of Compound 2 was prepared in the same manner as in Example 1. This solution was adjusted to pH 6.0 using disodium hydrogen phosphate, and this was freeze-dried. This freeze-dried preparation was designated as Example 13.

When the freeze-dried preparation thus obtained was redissolved in 3 mL of water for injection, the pH was 5.7.

Comparative Example 1

3 mL of a solution of Compound 1 was prepared in the same manner as in Example 1. This solution was adjusted to pH 1.0 using phosphoric acid, and this was freeze-dried. This freeze-dried preparation was designated as Comparative Example 1.

When the freeze-dried preparation thus obtained was redissolved in 3 mL of water for injection, the pH was 1.2.

Comparative Example 2

3 mL of a solution of Compound 1 was prepared in the same manner as in Example 1. This solution was adjusted to pH 2.0 using phosphoric acid, and this was freeze-dried. This freeze-dried preparation was designated as Comparative Example 2.

When the freeze-dried preparation thus obtained was redissolved in 3 mL of water for injection, the pH was 1.9.

Comparative Example 3

3 mL of a solution of Compound 1 was prepared in the same manner as in Example 1. This solution was adjusted to pH 7.0 using sodium hydrogen carbonate, and this was freeze-dried. This freeze-dried preparation was designated as Comparative Example 3.

When the freeze-dried preparation thus obtained was redissolved in 3 mL of water for injection, the pH was 8.1.

Comparative Example 4

3 mL of a solution of Compound 1 was prepared in the same manner as in Example 1. This solution was adjusted to pH 8.0 using sodium hydrogen carbonate, and this was freeze-dried. This freeze-dried preparation was designated as Comparative Example 4.

When the freeze-dried preparation thus obtained was redissolved in 3 mL of water for injection, the pH was 9.2.

Comparative Example 5

3 mL of a solution of Compound 2 was prepared in the same manner as in Example 1. This solution was adjusted to pH 1.0 using phosphoric acid, and this was freeze-dried. This freeze-dried preparation was designated as Comparative Example 5.

When the freeze-dried preparation thus obtained was redissolved in 3 mL of water for injection, the pH was 1.1.

Comparative Example 6

3 mL of a solution of Compound 2 was prepared in the same manner as in Example 1. This solution was adjusted to pH 2.0 using phosphoric acid, and this was freeze-dried. This freeze-dried preparation was designated as Comparative Example 6.

When the freeze-dried preparation thus obtained was redissolved in 3 mL of water for injection, the pH was 1.9.

Comparative Example 7

3 mL of a solution of Compound 2 was prepared in the same manner as in Example 1. This solution was adjusted to pH 8.0 using sodium hydrogen carbonate, and this was freeze-dried. This freeze-dried preparation was designated as Comparative Example 7.

When the freeze-dried preparation thus obtained was redissolved in 3 mL of water for injection, the pH was 9.2.

Example 14

3 mL of a solution of Compound 2 was prepared in the same manner as in Example 1. This solution was adjusted to pH 2.5 using citric acid, and this was freeze-dried. This freeze-dried preparation was designated as Comparative Example 8.

When the freeze-dried preparation thus obtained was redissolved in 3 mL of water for injection, the pH was 2.4.

TABLE 1

Table 1 List of pH at preparation and at redissolution of Examples and Comparative Examples

|  | Adjusted pH | pH at redissolution |
|---|---|---|
| Example 1 | — | 4.7 |
| Example 2 | 3.0 | 3.0 |
| Example 3 | 6.0 | 6.5 |
| Comparative Example 1 | 1.0 | 1.2 |
| Comparative Example 2 | 2.0 | 1.9 |
| Comparative Example 3 | 7.0 | 8.1 |
| Comparative Example 4 | 8.0 | 9.2 |

TABLE 2

Table 2 List of pH at preparation and at redissolution of Examples and Comparative Examples

|  | Adjusted pH | pH at redissolution |
|---|---|---|
| Example 4 | 3.0 | 2.9 |
| Example 5 | 3.5 | 3.5 |
| Example 6 | 4.5 | 4.5 |
| Example 7 | 6.0 | 6.9 |
| Example 8 | 4.0 | 4.2 |
| Example 9 | 4.0 | 4.2 |
| Example 10 | 3.2 | 3.2 |
| Example 11 | 4.0 | 4.2 |
| Example 12 | 5.0 | 5.0 |
| Example 13 | 6.0 | 5.7 |
| Comparative Example 5 | 1.0 | 1.1 |
| Comparative Example 6 | 2.0 | 1.9 |
| Comparative Example 7 | 8.0 | 9.2 |
| Example 14 | 2.5 | 2.4 |

Test Example 1; Change in Particle Size of Associative Aggregates Under Storage Conditions of 40° C./One Week 3 mL of water for injection was added to each of the freeze-dried preparations of Examples 1 to 3 and Comparative Examples 1 to 4, and a solution having a concentration of 1 mg/mL in terms of the EHC content was produced. The pH of this solution was measured. Subsequently, 3 mL of water for injection was further added thereto. 5 µL of this solution was taken, 480 µL of water for injection was added thereto, and this was used as a sample solution for particle size measurement. The sample solution was introduced into a measuring cell, and the average particle size was measured. This was designated as the initial particle size. A data analysis was conducted based on the Gaussian distribution (volume-weighted), and the data were described as the volume-weighted particle size. Meanwhile, the volume-weighted particle size is an average particle size based on weight fractions, and is defined by the following expression.

When it is assumed that particles having particle sizes of d1, d2, d3, . . . , di, . . . , and dk in an increasing order of particle size, exist in the numbers of n1, n2, n3, . . . , ni, . . . , and nk, respectively, and the volume per particle is designated as v1, v2, v3, . . . , vi, . . . , and vk, Volume-weighted particle size=$\Sigma(Vi \cdot di)/\Sigma(vi)$ Apart from this, the freeze-dried preparations of Examples 1 to 3 and Comparative Examples 1 to 4 were stored at 40° C. for one week under light-blocked conditions. Subsequently, a solution including each of the Examples and Comparative Examples at a concentration of 1 mg/mL in terms of the EHC content was produced using water for injection, and the pH of the solution was measured. Subsequently, samples were prepared in the same manner as in the case of the initial sample, and the particle size of the associative aggregates of each of the freeze-dried preparations was measured.

The measurement results of the initial solution pH and the initial particle size as well as the solution pH and the particle size after storage at 40° C./one week, and the change ratio of the particle size are summarized in Table 3.

The measuring instrument and the measurement conditions are presented below.

Measuring Instrument and Measurement Conditions
Measuring instrument: NICOMP Model 380 ZLS-S (manufactured by Particle Sizing Systems, LLC)
Cell temperature: 25° C.
Duration of measurement: 15 minutes

TABLE 3

Table 3 Results of Test Example 1

|  | pH at redissolution | | Volume-weighted particle size (nm) | | Change ratio of particle size |
|---|---|---|---|---|---|
|  | Initial | 40° C./1 W | Initial | 40° C./1 W |  |
| Example 1 | 4.7 | 4.6 | 43.9 | 39.3 | 0.90 |
| Example 2 | 3.0 | 3.1 | 38.1 | 26.2 | 0.69 |
| Example 3 | 6.5 | 5.7 | 41.9 | 23.7 | 0.57 |
| Comparative Example 1 | 1.2 | 1.2 | 129.7 | 799.7 | 6.17 |
| Comparative Example 2 | 1.9 | 1.9 | 39.4 | N.D.*[1] | — |
| Comparative Example 3 | 8.1 | 7.3 | 30.5 | 3683.0 | 120.75 |
| Comparative Example 4 | 9.2 | 8.4 | 29.5 | 4284.8 | 145.25 |

*[1]In Comparative Example 2, expansion of the particle size occurred at the time of measurement, and the measurement was not possible.

It was recognized from the results of Test Example 1 that the change ratios of the particle sizes of the freeze-dried preparations (Examples 1, 2 and 3) having a pH of 3.0 to 6.5 at the time of redissolution were as small as 0.57 to 0.90, and the preparations were stable during storage of the preparations, with less change in the associative aggregate-forming properties of the camptothecin derivative-bonded block copolymer as an active ingredient. In contrast, in regard to the freeze-dried preparations (Comparative Examples 1 and 2) having a solution pH of 1.9 or lower and the freeze-dried preparations (Comparative Examples 3 and 4) having a solution pH of 8 or higher, significant changes were observed in the particle size measured after storage at 40° C./one week. This indicates that the associative aggregate-forming properties of the active ingredient changed significantly, and it was revealed that the preparations had poor preparation storage stability.

The pharmaceutically active ingredient is a drug which achieves an increase in the antitumor effect and a decrease in side effects, by securing a pharmacokinetic behavior which is advantageous for manifesting the efficacy of the camptothecin derivative, based on the formation of associative aggregates. Therefore, the associative aggregate-forming ability is an important physical property for the relevant pharmaceutically active ingredient, and it was shown that, when the solution pH of the freeze-dried preparations was set in the range of 3 to 6.5, it was effective for stabilization of the preparations.

Test Example 2: Change in Molecular Weight of Associative Aggregates Under Storage Conditions of 40° C./One Week 3 mL of water for injection was added to each of the freeze-dried preparations of Examples 1 to 3 and Comparative Examples 1 to 4, and a solution having a concentration of 1 mg/mL in terms of the EHC content was produced. The pH of this solution was measured. Subsequently, 3 mL of water for injection was further added thereto. The average molecular weight of the associative aggregates in this solution was measured by a SEC-MALS method. This was designated as the initial average molecular weight. The measuring instrument and the measurement conditions are presented below. Meanwhile, the average molecular weight of the associative aggregates measured according to the SEC-MALS method has the same meaning as the total molecular weight of the associates related to the present invention, and thus hereinafter, the total molecular weight of the associate will be referred to as the average molecular weight.

Apart from this, the freeze-dried preparations of Examples 1 to 3 and Comparative Examples 1 to 4 were stored at 40° C. for one week under light-blocked conditions. Subsequently, a solution including each of the Examples and Comparative Examples at a concentration of 1 mg/mL in terms of the EHC content was prepared using water for injection, and the pH of the solution was measured. Subsequently, samples were prepared in the same manner as in the case of the initial sample, and the average molecular weight of the associative aggregates in the solution of each of the freeze-dried preparations was measured.

The measurement results of the initial solution pH and the initial average molecular weight as well as the solution pH and the average molecular weight after storage at 40° C./one week, and the change ratio of the average molecular weight are summarized in Table 4.

Measuring Instrument and Measurement Conditions
GPC system: SHODEX GPC-101 (manufactured by Shoko Scientific Co., Ltd.)
Column used: SHODEX OHPAK SB-806M HQ 300 mm×8.0 mm$^{I.D.}$
Light scattering detector: DAWN 8+(manufactured by Wyatt Technology Corp.)
Data processing apparatus: Shimadzu C-R7A (UV, RI)
ASTRA for Windows 5.3.4 (DAWN)
Cell temperature: 40° C.
Duration of measurement: 20 minutes
Mobile phase solvent: 50 mM aqueous solution of NaCl
Mobile phase flow rate: 1 mL/min

TABLE 4

Table 4 Change ratios of average molecular weights of various redissolved micellar samples

| | pH at redissolution | | Average molecular weight (millions) | | Change ratio of average molecular weight (millions) |
|---|---|---|---|---|---|
| | Initial | 40° C. for one week | Initial | 40° C. for one week | |
| Example 1 | 4.7 | 4.6 | 9.6 | 7.9 | 17.7 |
| Example 2 | 3.0 | 3.1 | 9.6 | 7.7 | 19.8 |
| Example 3 | 6.5 | 5.7 | 11.1 | 6.5 | 41.4 |

TABLE 4-continued

Table 4 Change ratios of average molecular weights of various redissolved micellar samples

| | pH at redissolution | | Average molecular weight (millions) | | Change ratio of average molecular weight (millions) |
|---|---|---|---|---|---|
| | Initial | 40° C. for one week | Initial | 40° C. for one week | |
| Comparative Example 1 | 1.2 | 1.2 | 0.9 | N.D.*[2] | — |
| Comparative Example 2 | 1.9 | 1.9 | 8.4 | 2.4 | 71.4 |
| Comparative Example 3 | 8.1 | 7.3 | 4.4 | 4.3 | 2.3 |
| Comparative Example 4 | 9.2 | 8.4 | 3.2 | 0.8 | 75.0 |

*[2]Associative aggregates were not clearly recognized at the time of measurement of Comparative Example 1 after one week at 40° C., and thus the measurement was not possible.

It was recognized from the results of Test Example 2 that the change ratios of the measured values of molecular weight related to the associative aggregates of the freeze-dried preparations (Examples 1, 2 and 3) having a pH of 3.0 to 6.5 at the time of redissolution were 50% or less, and the preparations were stable during storage of the preparations, with less change in the associative aggregate-forming properties of the camptothecin derivative-bonded block copolymer as an active ingredient. Particularly, it was shown that Examples 1 and 2 were very stable preparations having molecular weight change ratios for the associative aggregates of 20% or less. In contrast, in regard to the freeze-dried preparations (Comparative Examples 1 and 2) having a solution pH of 1.9 or lower, significant changes were observed in the average molecular weight values of the associative aggregates measured after storage at 40° C./one week. Furthermore, for the freeze-dried preparations (Comparative Examples 3 and 4) having a solution pH of 8 or higher, the initial molecular weights of the associative aggregates were small, demonstrating that the associative aggregate-forming properties of the active ingredient were greatly different even in initial values. Therefore, in regard to the freeze-dried preparations related to Comparative Examples, it was revealed that the associative aggregate-forming performance of the active ingredient was significantly changed.

From the above results, it was shown that, in order to stably maintain the associative aggregate forming performance, which is an important physical property of the pharmaceutically active ingredient, it is preferable to set the pH of the solution of the freeze-dried preparation in the range of 3.0 to 6.5.

Test Example 3; Change in Particle Size of Associative Aggregates of Examples and Comparative Examples Under Storage Conditions of 40° C./One Week 3 mL of water for injection was added to each of the preparations of Examples 4 to 14 and Comparative Examples 5 to 7 immediately after freeze-drying, and a solution having a concentration of 1 mg/mL in terms of the EHC content was prepared. The pH of this solution was measured. Subsequently, 3 mL of water for injection was further added thereto. 5 μL of this solution was taken, 480 μL of water for injection was added thereto, and this was used as a sample solution for particle size measurement. The sample solution was introduced into a measuring cell, and the average particle size was measured. This was designated as the initial particle size. A data analysis was conducted based on the Gaussian distribution (volume-weighted). The same measuring instrument and the measurement conditions as those of Test Example 1 were employed.

Apart from this, the freeze-dried preparations of Examples 4 to 14 and Comparative Examples 5 to 7 were stored at 40° C. for one week under light-blocked conditions. Subsequently, a solution including each of the Examples and Comparative Examples at a concentration of 1 mg/mL in terms of the EHC content was produced using water for injection, and the pH of the solution was measured. Subsequently, samples were prepared in the same manner as in the case of the initial sample, and the particle size of the associative aggregates of each of the freeze-dried preparations was measured.

The measurement results of the initial solution pH and the initial particle size, and the solution pH and the particle size after storage at 40° C./one week, and the change ratio of the particle size are summarized in Table 5.

TABLE 5

Table 5 Change ratios of average particle sizes of various redissolved micellar samples

|  | pH at redissolution | | Volume-weighted particle size (nm) | | Change ratio of |
| --- | --- | --- | --- | --- | --- |
|  | Initial | 40° C./ 1 W | Initial | 40° C./ 1 W | particle size |
| Example 4 | 2.9 | 3.0 | 28.7 | 25.4 | 0.89 |
| Example 5 | 3.5 | 3.5 | 31.0 | 26.4 | 0.85 |
| Example 6 | 4.5 | 4.5 | 25.9 | 21.7 | 0.84 |
| Example 7 | 6.9 | 6.6 | 24.8 | 27.4 | 1.10 |
| Example 8 | 4.2 | 4.3 | 50.8 | 46.5 | 0.92 |
| Example 9 | 4.2 | 4.3 | 41.7 | 44.0 | 1.06 |
| Example 10 | 3.2 | 3.2 | 26.3 | 26.6 | 1.01 |
| Example 11 | 4.2 | 4.1 | 29.0 | 28.9 | 1.00 |
| Example 12 | 5.0 | 5.0 | 30.2 | 32.0 | 1.06 |
| Example 13 | 5.7 | 5.5 | 36.9 | 34.8 | 0.94 |
| Comparative Example 5 | 1.1 | 1.1 | 76.9 | 516.5 | 6.72 |
| Comparative Example 6 | 1.9 | 2.0 | 23.5 | N.D.*[3] | — |
| Comparative Example 7 | 9.2 | 9.2 | 22.5 | N.D.*[3] | — |
| Example 14 | 2.4 | 2.5 | 24.7 | 31.5 | 1.28 |

*[3]In Comparative Examples 6 and 7, expansion of the particle size occurred at the time of measurement, and the particle size was not measurable.

Test Example 4; Change in Particle Size of Associative Aggregates of Example and Comparative Examples Under Storage Conditions of 40° C./Two Weeks 3 mL of water for injection was added to each of the preparations of Examples 4 to 9 and Comparative Examples 5 to 7 immediately after freeze-drying, and a solution having a concentration of 1 mg/mL in terms of the EHC content was prepared. The pH of this solution was measured. Subsequently, 3 mL of water for injection was further added thereto. 5 μL of this solution was taken, 480 μL of water for injection was added thereto, and this was used as a sample solution for particle size measurement. The sample solution was introduced into a measuring cell, and the average particle size was measured. This was designated as the initial particle size. A data analysis was conducted based on the Gaussian distribution (volume-weighted). The same measuring instrument and the measurement conditions as those of Test Example 1 were employed.

Apart from this, the freeze-dried preparations of Examples 4 to 9 and Comparative Examples 5 to 7 were stored at 40° C. for two weeks under light-blocked conditions. Subsequently, a solution including each of the Examples and Comparative Examples at a concentration of 1 mg/mL in terms of the EHC content was produced using water for injection, and the solution pH was measured. Subsequently, samples were prepared in the same manner as in the case of the initial sample, and the particle size of the associative aggregates of each of the freeze-dried preparations was measured.

The measurement results of the initial solution pH and the initial particle size as well as the solution pH and the particle size after storage at 40° C./two weeks, and the change ratio of the particle size are summarized in Table 6.

TABLE 6

Table 6 Change ratios of average particle sizes of various redissolved micellar samples

|  | pH at redissolution | | Volume-weighted particle size (nm) | | Change ratio of |
| --- | --- | --- | --- | --- | --- |
|  | Initial | 40° C./ 2 W | Initial | 40° C./ 2 W | particle size |
| Example 4 | 2.9 | 3.0 | 28.7 | 26.7 | 0.93 |
| Example 5 | 3.5 | 3.5 | 31.0 | 36.9 | 1.19 |
| Example 6 | 4.5 | 4.4 | 25.9 | 22.8 | 0.88 |
| Example 7 | 6.9 | 6.8 | 24.8 | 27.2 | 1.10 |
| Example 8 | 4.2 | 4.2 | 50.8 | 41.0 | 0.81 |
| Example 9 | 4.2 | 4.3 | 41.7 | 48.7 | 1.17 |
| Comparative Example 5 | 1.1 | 1.1 | 76.9 | 1334.2 | 17.35 |
| Comparative Example 6 | 1.9 | 2.0 | 23.5 | N.D.*[4] | — |
| Comparative Example 7 | 9.2 | 9.2 | 22.5 | N.D.*[4] | — |

*[4]In Comparative Examples 6 and 7, expansion of the particle size occurred at the time of measurement, and the particle size was not measurable.

The results of Test Examples 3 and 4 demonstrate that the change ratios of the particle sizes of the freeze-dried preparations (Examples 4 to 14) having a pH of 2.4 to 7.0 at the time of redissolution at a time point after storage at 40° C./one week were 0.84 to 1.28, and that the change ratios of the particle sizes of the freeze-dried preparations (Examples 4 to 9) at a time point after storage at 40° C./two weeks were as small as 0.81 to 1.19. Therefore, it was found that the preparations were stable during storage of the preparations, with less change in the associative aggregate-forming properties of the camptothecin derivative-bonded block copolymer as an active ingredient. In contrast, in regard to the freeze-dried preparations (Comparative Examples 5 and 6) having a solution pH of 1.9 or lower and the freeze-dried preparation (Comparative Example 7) having a solution pH of 9 or higher, significant changes were observed in the particle size measured during storage at 40° C. for one week and two weeks. This shows that the associative aggregate-forming properties of the active ingredient changed significantly, and as a result, it was revealed that the preparations had poor storage stability. The relevant pharmaceutically active ingredient is a drug which achieves an increase in the antitumor effect and a decrease in side effects, by securing a pharmacokinetic behavior advantageous for manifesting the efficacy of the camptothecin derivative based on the formation of associative aggregates. Therefore, the associative aggregate-forming ability is an important physical property for the relevant pharmaceutically active ingredient, and similarly to the results of Test Example 1, it was shown that when the solution pH of the freeze-dried preparations was set in the range of 3.0 to 6.5, it was effective for stabilization of the preparations.

Test Example 5; Change in Average Molecular Weight of Associative Aggregates of Examples and Comparative Examples Under Storage Conditions of 40° C./One Week 3 mL of water for injection was added to each of the freeze-dried preparations of Examples 4 to 14 and Comparative Examples 5 to 7, and a solution having a concentration of 1 mg/mL in terms of the EHC content was prepared. The pH of this solution was measured. Subsequently, 3 mL of water for injection was further added thereto. The average molecular weight of the associative aggregates in this solution was measured by a SEC-MALS method. This was designated as the initial average molecular weight of the associative aggregates. The same measuring instrument and measurement conditions as those of Test Example 2 were employed.

Apart from this, the freeze-dried preparations of Examples 4 to 14 and Comparative Examples 5 to 7 were stored at 40° C. for one week under light-blocked condition. Subsequently, a solution including each of the Examples and Comparative Examples at a concentration of 1 mg/mL in terms of the EHC content was produced using water for injection, and the pH of the solution was measured. Subsequently, samples were prepared in the same manner as in the case of the initial sample, and the average molecular weight of the associative aggregates in the solution of each of the freeze-dried preparations was measured.

The measurement results of the initial solution pH and the initial average molecular weight, and the solution pH and the average molecular weight after storage at 40° C./one week, and the change ratio of the average molecular weight are summarized in Table 7.

TABLE 7

Table 7 Change ratios of average molecular weights of various redissolved micellar samples

|  | pH at redissolution | | Average molecular weight (millions) | | Average molecular weight Change ratio |
| --- | --- | --- | --- | --- | --- |
|  | Initial | 40° C./1 W | Initial | 40° C./1 W |  |
| Example 4 | 2.9 | 3.0 | 5.8 | 5.1 | 12.1 |
| Example 5 | 3.5 | 3.5 | 5.2 | 5.1 | 2.0 |
| Example 6 | 4.5 | 4.5 | 5.1 | 5.2 | 2.0 |
| Example 7 | 6.9 | 6.6 | 3.7 | 3.4 | 8.1 |
| Example 8 | 4.2 | 4.3 | 16.1 | 14.6 | 9.3 |
| Example 9 | 4.2 | 4.3 | 13.4 | 13.6 | 1.5 |
| Example 10 | 3.2 | 3.2 | 5.8 | 5.4 | 6.9 |
| Example 11 | 4.2 | 4.1 | 5.6 | 5.7 | 1.8 |
| Example 12 | 5.0 | 5.0 | 7.0 | 6.6 | 5.7 |
| Example 13 | 5.7 | 5.5 | 5.7 | 4.5 | 21.1 |
| Comparative Example 5 | 1.1 | 1.1 | 0.7 | N.D.*5 | — |
| Comparative Example 6 | 1.9 | 2.0 | 7.7 | 3.4 | 55.8 |
| Comparative Example 7 | 9.2 | 9.2 | 9.2 | 0.3 | 86.4 |
| Example 14 | 2.4 | 2.5 | 6.8 | 5.0 | 26.5 |

*5Associative aggregates were not clearly recognized in the measurement of Comparative Example 5 after one week at 40° C., and the measurement was not possible.

Test Example 6; Change in Average Molecular Weight of Associative Aggregates of Examples and Comparative Examples Under Storage Conditions of 40° C./Two Weeks 3 mL of water for injection was added to each of the freeze-dried preparations of Examples 4 to 9 and Comparative Examples 5 to 7, and a solution having a concentration of 1 mg/mL in terms of the EHC content was prepared. The pH of this solution was measured. Subsequently, 3 mL of water for injection was further added thereto. The average molecular weight of the associative aggregates in this solution was measured by a SEC-MALS method. This was designated as the initial average molecular weight of the associative aggregates. The same measuring instrument and measurement conditions as those of Test Example 2 were employed.

Apart from this, the freeze-dried preparations of Examples 4 to 9 and Comparative Examples 5 to 7 were stored at 40° C. for two week under light-blocked condition. Subsequently, a solution of each of the Examples and Comparative Examples comprising EHC at a concentration of 1 mg/mL in terms of the EHC content was prepared using water for injection, and the pH of the solution was measured. Subsequently, samples were prepared in the same manner as in the case of the initial sample, and the average molecular weight of the associative aggregates in the solution of each of the freeze-dried preparations was measured.

The measurement results of the initial solution pH and the initial particle size, and the solution pH and the particle size after storage at 40° C./two weeks, and the change ratio of the particle size are summarized in Table 8.

TABLE 8

Table 8 Change ratios of average particle sizes of various redissolved micellar samples

|  | pH at redissolution | | Average molecular weight (millions) | | Change ratio of average molecular weight (millions) |
| --- | --- | --- | --- | --- | --- |
|  | Initial | 40° C./ 2 W | Initial | 40° C./ 2 W |  |
| Example 4 | 2.9 | 3.0 | 5.8 | 3.5 | 39.7 |
| Example 5 | 3.5 | 3.5 | 5.2 | 4.1 | 21.2 |
| Example 6 | 4.5 | 4.4 | 5.1 | 3.5 | 31.4 |
| Example 7 | 6.9 | 6.8 | 3.7 | 3.4 | 8.1 |
| Example 8 | 4.2 | 4.2 | 16.1 | 13.6 | 15.5 |
| Example 9 | 4.2 | 4.3 | 13.4 | 13.6 | 1.5 |
| Comparative Example 5 | 1.1 | 1.1 | 0.7 | N.D.*6 | — |
| Comparative Example 6 | 1.9 | 2.0 | 7.7 | 1.6 | 79.2 |
| Comparative Example 7 | 9.2 | 9.2 | 2.2 | 0.1 | 95.5 |

*6Clear associative aggregates were not recognized in the measurement of Comparative Example 5 after two weeks at 40° C., and the measurement was not possible.

The results of Test Examples 5 and 6 demonstrate that after storage at 40° C. for one week and after storage at 40° C. for two weeks, the change ratios of the measured values of average molecular weight related to the associative aggregates of the freeze-dried preparations (Examples 4 to 9) having a pH of 2.4 to 7.0 at the time of redissolution were 50% or less, and it was found that the preparations were stable during storage of the preparation, with less change in the associative aggregate-forming properties of the camptothecin derivative-bonded block copolymer as an active ingredient. In contrast, for the freeze-dried preparations (Comparative Examples 5 and 6) having a solution pH of 1.9 or lower, significant changes were observed in the average molecular weight values of the associative aggregates measured during storage at 40° C./one week. Furthermore, for the freeze-dried preparation (Comparative Example 7) having a solution pH of 9 or higher, the results show that the initial total molecular weight of the associative aggregates was small, demonstrating that the associative aggregate-forming properties of the active ingredient are significantly different even in initial value at the initial time. Therefore, it was revealed that, in the freeze-dried preparations related to Comparative Examples, the associative aggregate-forming performance of the active ingredient was significantly changed. Therefore, similarly to the results of Test Example 2, it was indicated that, in order to stably maintain the associative aggregate forming performance, which is an important physical property of the relevant pharmaceutically active ingredient, it is necessary to set the solution pH of the freeze-dried preparation to in the range of 3.0 to 6.5.

Test Example 7; Change in Light Scattering Intensity of Associative Aggregates of Examples and Comparative Examples Under Storage Conditions of 40° C./One Week 3 mL of water for injection was added to each of the freeze-dried preparations of Examples 4 to 13 and Comparative Examples 5 to 7, and a solution having a concentration of 1 mg/mL in terms of the EHC content was prepared. The pH of this solution was measured. Subsequently, 3 mL of water for injection was further added thereto. The amount of scattered light for the associative aggregates in this solution was measured by a static light scattering method (SLS method). This was designated as the initial amount of scattered light. The measuring instrument and the measurement conditions are presented below.

Apart from this, the freeze-dried preparations of Examples 4 to 13 and Comparative Examples 5 to 7 were stored at 40° C. for one week under light-blocked conditions. Subsequently, a solution of each of the Examples and Comparative Examples comprising EHC at a concentration of 1 mg/mL in terms of the EHC content was prepared using water for injection, and the pH of the solution was measured. Subsequently, samples were prepared in the same manner as in the case of the initial sample, and the amount of scattered light for the associative aggregates in the solution of each of the freeze-dried preparations was measured.

The measurement results of the initial solution pH and the initial amount of scattered light as well as the solution pH and the amount of scattered light after storage at 40° C./one week are summarized in Table 9.

Measuring Instrument and Measurement Conditions

Light scattering photometer: DLS-8000DL (manufactured by Otsuka Electronics Co., Ltd.)
Contra-roller: LS-81 (manufactured by Otsuka Electronics Co., Ltd.)
Pump contra-roller: LS-82 (manufactured by Otsuka Electronics Co., Ltd.)
High sensitivity differential refractometer: DRM-3000 (manufactured by Otsuka Electronics Co., Ltd.)
Circulating thermostatic tank: LAUDA E200
Wavelength: 632.8 nm (He—Ne)
Angle: 900
Ph1: OPEN
Ph2: SLIT
ND Filter: 10%
Dust-cut setting: 10
Measurement temperature: 25° C.

TABLE 9

Table 9 Change ratios of amounts of scattered light of various redissolved micellar samples

|  | pH at redissolution | | Amount of light (cps) | | Change ratio in amount of scattered light |
| --- | --- | --- | --- | --- | --- |
|  | Initial | 40° C./ 1 W | Initial | 40° C./ 1 W |  |
| Example 4 | 2.9 | 3.0 | 17142 | 9916 | 0.58 |
| Example 5 | 3.5 | 3.5 | 15278 | 8701 | 0.57 |

TABLE 9-continued

Table 9 Change ratios of amounts of scattered light of various redissolved micellar samples

|  | pH at redissolution | | Amount of light (cps) | | Change ratio in amount of scattered light |
| --- | --- | --- | --- | --- | --- |
|  | Initial | 40° C./ 1 W | Initial | 40° C./ 1 W |  |
| Example 6 | 4.5 | 4.5 | 17075 | 7482 | 0.44 |
| Example 7 | 6.9 | 6.6 | 8361 | 8441 | 1.01 |
| Example 8 | 4.2 | 4.3 | 47189 | 43480 | 0.92 |
| Example 9 | 4.2 | 4.3 | 50566 | 49842 | 0.99 |
| Example 10 | 3.2 | 3.2 | 17819 | 13166 | 0.74 |
| Example 11 | 4.2 | 4.1 | 17154 | 11785 | 0.69 |
| Example 12 | 5.0 | 5.0 | 13437 | 6189 | 0.46 |
| Example 13 | 5.7 | 5.5 | 10893 | 7842 | 0.63 |
| Comparative Example 5 | 1.1 | 1.1 | 4808 | 223915 | 46.57 |
| Comparative Example 6 | 1.9 | 2.0 | 14287 | 77661 | 5.44 |
| Comparative Example 7 | 9.2 | 9.2 | 4582 | 1238 | 0.27 |

Test Example 8; Change in Light Scattering Intensity of Associative Aggregates of Examples and Comparative Examples Under Storage Conditions of 40° C./Two Weeks 3 mL of water for injection was added to each of the freeze-dried preparations of Examples 4 to 9 and Comparative Examples 5 to 7, and a solution having a concentration of 1 mg/mL in terms of the EHC content was produced. The pH of this solution was measured. Subsequently, 3 mL of water for injection was further added thereto. The amount of scattered light for the associative aggregates in this solution was measured by a static light scattering method (SLS method). This was designated as the initial amount of scattered light. The same measuring instrument and measurement conditions as those of Test Example 7 were employed.

The freeze-dried preparations of Examples 4 to 9 and Comparative Examples 5 to 7 were stored at 40° C. for two weeks under light-blocked conditions. Subsequently, a solution of each of the Examples and Comparative Examples at a concentration of 1 mg/mL in terms of the EHC content was prepared to comprise EHC using water for injection, and the solution pH was measured. Subsequently, samples were prepared in the same manner as in the case of the initial sample, and the amount of scattered light for the associative aggregates in the solution of each of the freeze-dried preparations was measured.

The measurement results of the initial solution pH and the initial amount of scattered light as well as the solution pH and the amount of scattered light after storage at 40° C./two weeks, and the change ratio of the amount of scattered light are summarized in Table 10.

TABLE 10

Table 10 Change ratios of amounts of scattered light of various redissolved micellar samples

|  | pH on redissolution | | Amount of light (cps) | | Change ratio in scattered light |
| --- | --- | --- | --- | --- | --- |
|  | Initial | 40° C./ 2 W | Initial | 40° C./ 2 W |  |
| Example 4 | 2.9 | 3.0 | 17142 | 10624 | 0.62 |
| Example 5 | 3.5 | 3.5 | 15278 | 18721 | 1.23 |

TABLE 10-continued

Table 10 Change ratios of amounts of scattered light of various redissolved micellar samples

| | pH on redissolution | | Amount of light (cps) | | Change ratio in |
|---|---|---|---|---|---|
| | Initial | 40° C./ 2 W | Initial | 40° C./ 2 W | scattered light |
| Example 6 | 4.5 | 4.4 | 17075 | 8771 | 0.51 |
| Example 7 | 6.9 | 6.8 | 8361 | 11571 | 1.38 |
| Example 8 | 4.2 | 4.2 | 47189 | 43850 | 0.93 |
| Example 9 | 4.2 | 4.3 | 50566 | 43730 | 0.86 |
| Comparative Example 5 | 1.1 | 1.1 | 4808 | 297059 | 61.78 |
| Comparative Example 6 | 1.9 | 2.0 | 14287 | 251260 | 17.59 |
| Comparative Example 7 | 9.2 | 9.2 | 4582 | 583 | 0.13 |

From the results of Test Examples 7 and 8, the change ratios of the amounts of scattered light for the freeze-dried preparations (Examples 4 to 13) having a pH of 2.9 to 6.9 at the time of redissolution were 0.44 to 1.01 at a time point after storage at 40° C./one week, and the change ratios of the amounts of scattered light for the freeze-dried preparations (Examples 4 to 9) were 0.62 to 1.38 at a time point after storage at 40° C./two weeks. Measurements of the average particle size and the total molecular weight (average molecular weight) of Test Examples 1 to 6 are values calculated from the amount of dynamic scattered light obtained using laser light. On the other hand, in Test Examples 7 and 8, the amount of static scattered light was measured. Therefore, the value of the amount of scattered light may serve as an index for the associative-forming properties of the camptothecin derivative-bonded block copolymer. Thus, any change in the associate-forming properties may be measured by directly using the amount of scattered light. It was acknowledged that a pharmaceutical preparation comprising the camptothecin derivative-bonded block copolymer of the present invention as an active ingredient is a stable preparation with less change in the associate-forming properties during storage of the preparation.

From the results of Test Example 7, a pharmaceutical preparation comprising the camptothecin derivative-bonded block copolymer of the present invention as an active ingredient may be defined as a pharmaceutical preparation in which, after storage at 40° C. for one week under light-blocked conditions, the change ratio of the amount of scattered light for the associates of the pharmaceutical preparation is from 0.4 to 1.5. Furthermore, from the results of Test Example 8, a pharmaceutical preparation comprising the camptothecin derivative-bonded block copolymer of the present invention as an active ingredient may be defined as a pharmaceutical preparation in which, after storage at 40° C. for two weeks under light-blocked conditions, the change ratio of the amount of scattered light for the associates of the pharmaceutical preparation is from 0.4 to 1.5.

Furthermore, based on the results of Test Examples 1 to 8, a pharmaceutical preparation comprising the camptothecin derivative-bonded block copolymer of the present invention as an active ingredient may be defined as a pharmaceutical preparation in which, after storage at 40° C. for one week under light-blocked conditions, the change ratio of the total molecular weight of the associates is 50% or less, the change ratio of the particle size of the associates measured by a dynamic light scattering method is from 0.25 times to 5 times, and the change ratio of the amount of scattered light for the associates is from 0.4 to 1.5.

From the results described above, it is acknowledged that a pharmaceutical preparation comprising the camptothecin derivative-bonded block copolymer of the present invention as an active ingredient is a pharmaceutical preparation having excellent storage stability, with less change in the associate-forming properties during storage of the preparation.

The invention claimed is:

1. A pharmaceutical preparation comprising a block copolymer represented by general formula (1), the block copolymer comprising a polyethylene glycol segment linked to a polyglutamic acid segment comprising a glutamic acid unit having a camptothecin derivative bonded thereto:

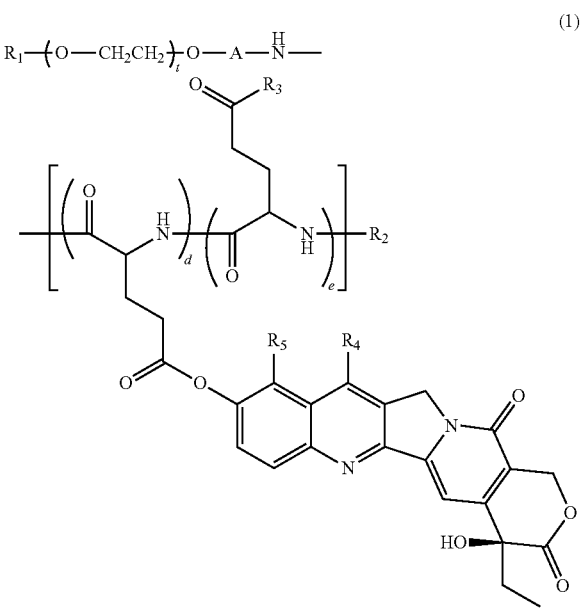

wherein $R_1$ represents a hydrogen atom or a (C1-C6) alkyl group optionally substituted with a substituent; A represents a (C1-C6) alkylene group; $R_2$ represents any one selected from the group consisting of a hydrogen atom, a (C1-C6) acyl group optionally substituted with a substituent, and a (C1-C6) alkoxycarbonyl group optionally substituted with a substituent; $R_3$ represents a hydroxyl group and/or —N($R_6$)CONH($R_7$); $R_6$ and $R_7$ may be identical or different and each represent a (C1-C8) alkyl group optionally substituted with a tertiary amino group; $R_4$ represents any one selected from the group consisting of a hydrogen atom, a (C1-C6) alkyl group optionally substituted with a substituent, and a silyl group optionally substituted with a substituent; $R_5$ represents a hydrogen atom or a (C1-C6) alkyl group optionally substituted with a substituent; t represents an integer from 90 to 340; d and e each represent an integer, (d+e) represents an integer from 8 to 40; the proportion of d with respect to (d+e) is 20% to 70%, and the proportion of e is 30% to 80%; and the polyglutamic acid segment has a polyglutamic acid segment structure including a glutamic acid unit having the camptothecin derivative bonded thereto and a glutamic acid unit having a $R_3$ group bonded thereto, with the glutamic acid units being each independently arranged in a random manner, wherein a plurality of molecules of the block copolymer form associates in an aqueous solution of the pharmaceutical preparation, wherein the pharmaceutical preparation comprises a pH adjusting agent, wherein, when the pharmaceutical preparation is made into an aqueous solution containing the camptothecin derivative at a concentration of 1 mg/mL, the pH of the aqueous solution is 3.0 to 5.0, wherein the change ratio of the total molecular weight of the associates of the pharmaceutical preparation obtained after storage of the pharmaceutical preparation at 40° C. for one week under light-blocked conditions is 50% or less, and wherein the pharmaceutical preparation is a freeze-dried preparation.

2. The pharmaceutical preparation according to claim 1, further comprising a sugar and/or a polyol.

3. A pharmaceutical preparation comprising a block copolymer represented by general formula (1), the block copolymer comprising a polyethylene glycol segment linked to a polyglutamic acid segment containing a glutamic acid unit having a camptothecin derivative bonded thereto:

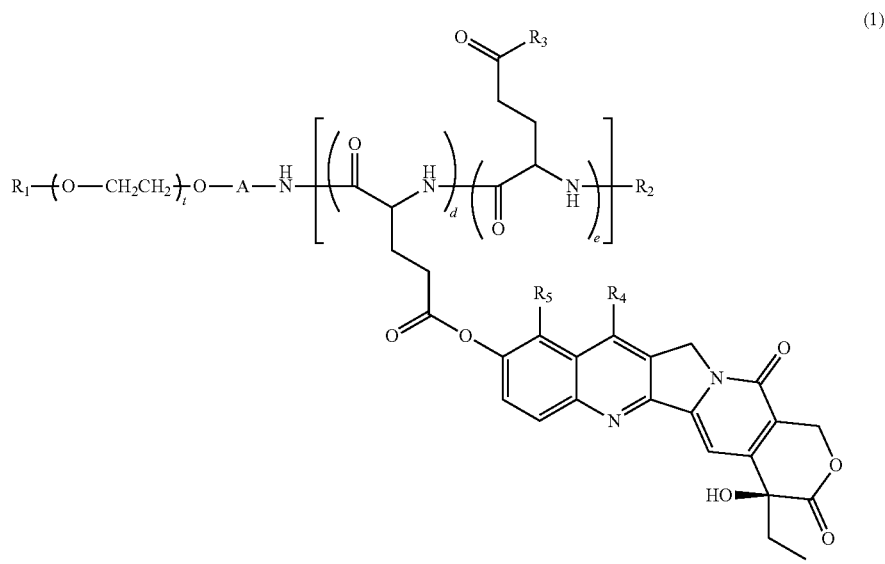

(1)

wherein $R_1$ represents a hydrogen atom or a (C1-C6) alkyl group optionally substituted with a substituent; A represents a (C1-C6) alkylene group; $R_2$ represents any one selected from the group consisting of a hydrogen atom, a (C1-C6) acyl group optionally substituted with a substituent, and a (C1-C6) alkoxycarbonyl group optionally substituted with a substituent; $R_3$ represent a hydroxyl group and/or —N($R_6$)CONH($R_7$); $R_6$ and $R_7$ may be identical or different and each represent a (C1-C8) alkyl group optionally substituted with a tertiary amino group; $R_4$ represents any one selected from the group consisting of a hydrogen atom, a (C1-C6) alkyl group optionally substituted with a substituent, and a silyl group optionally substituted with a substituent; $R_5$ represents a hydrogen atom or a (C1-C6) alkyl group optionally substituted with a substituent; t represents an integer from 90 to 340; d and e each represent an integer, (d+e) represents an integer from 8 to 40; the proportion of d with respect to (d+e) is 20% to 70%, and the proportion of e is 30% to 80%; and the polyglutamic acid segment has a polyglutamic acid segment structure including a glutamic acid unit having the camptothecin derivative bonded thereto and a glutamic acid unit having a $R_3$ group bonded thereto, with the glutamic acid units being each independently arranged in a random manner, wherein a plurality of molecules of the block copolymer form associates in an aqueous solution of the pharmaceutical preparation, wherein the pharmaceutical preparation comprises a pH adjusting agent, wherein, when the pharmaceutical preparation is made into an aqueous solution containing the camptothecin derivative at a concentration of 1 mg/mL, the pH of the aqueous solution is 3.0 to 5.0, wherein the change ratio of the particle size of the associates of the pharmaceutical preparation measured by a dynamic light scattering method after storage of the pharmaceutical preparation at 40° C. for one week under light-blocked conditions is from 0.25 times to 5 times, and wherein the pharmaceutical preparation is a freeze-dried preparation.

4. The pharmaceutical preparation according to claim 3, further comprising a sugar and/or a polyol.

5. A pharmaceutical preparation comprising a block copolymer represented by general formula (1), the block copolymer comprising a polyethylene glycol segment linked to a polyglutamic acid segment containing a glutamic acid unit having a camptothecin derivative bonded thereto:

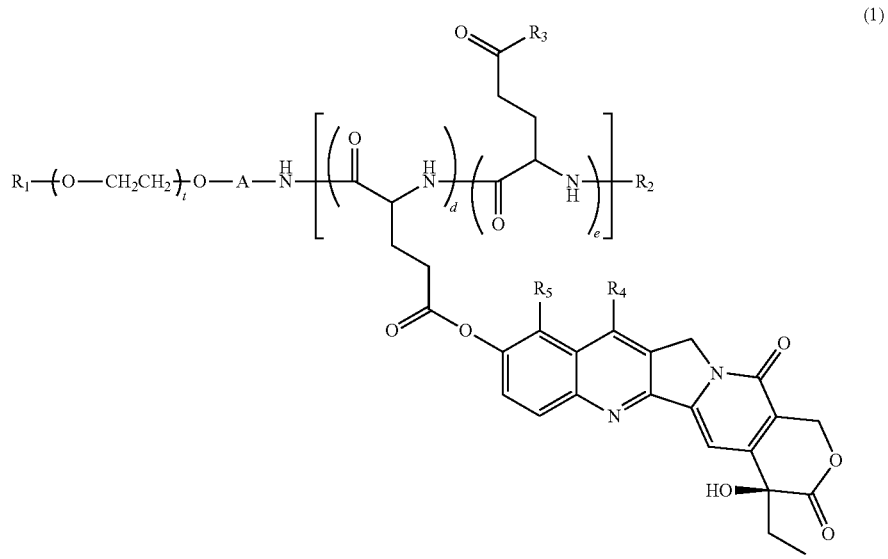

(1)

wherein $R_1$ represents a hydrogen atom or a (C1-C6) alkyl group optionally substituted with a substituent; A represents a (C1-C6) alkylene group; $R_2$ represents any one selected from the group consisting of a hydrogen atom, a (C1-C6) acyl group optionally substituted with a substituent, and a (C1-C6) alkoxycarbonyl group optionally substituted with a substituent; $R_3$ represent a hydroxyl group and/or —N($R_6$)CONH($R_7$); $R_6$ and $R_7$ may be identical or different and each represent a (C1-C8) alkyl group optionally substituted with a tertiary amino group; $R_4$ represents any one selected from the group consisting of a hydrogen atom, a (C1-C6) alkyl group optionally substituted with a substituent, and a silyl group optionally substituted with a substituent; $R_5$ represents a hydrogen atom or a (C1-C6) alkyl group optionally substituted with a substituent; t represents an integer from 90 to 340; d and e each represent an integer, (d+e) represents an integer from 8 to 40; the proportion of d with respect to (d+e) is 20% to 70%, and the proportion of e is 30% to 80%; and the polyglutamic acid segment has a polyglutamic acid segment structure including a glutamic acid unit having the camptothecin derivative bonded thereto and a glutamic acid unit having a $R_3$ group bonded thereto, with the glutamic acid units being each independently arranged in a random manner, wherein a plurality of molecules of the block copolymer form associates in an aqueous solution of the pharmaceutical preparation, wherein the pharmaceutical preparation comprises a pH adjusting agent, wherein, when the pharmaceutical preparation is made into an aqueous solution containing the camptothecin derivative at a concentration of 1 mg/mL, the pH of the aqueous solution is 3.0 to 5.0, wherein the change ratio of the total molecular weight of the associates of the pharmaceutical preparation obtainable after storage of the pharmaceutical preparation at 40° C. for one week under light-blocked conditions is 50% or less, wherein the change ratio of the particle size of the associates of the pharmaceutical preparation measured by a dynamic light scattering method after storage of the pharmaceutical preparation at 40° C. for one week under light-blocked conditions is from 0.25 times to 5 times, and wherein the pharmaceutical preparation is a freeze-dried preparation.

6. The pharmaceutical preparation according to claim 5, further comprising a sugar and/or a polyol.

* * * * *